(12) United States Patent
Shim et al.

(10) Patent No.: US 9,974,482 B2
(45) Date of Patent: May 22, 2018

(54) MOBILE TERMINAL AND METHOD OF CONTROLLING THE SAME

(71) Applicant: LG ELECTRONICS INC., Seoul (KR)

(72) Inventors: Hongjo Shim, Seoul (KR); Hyunok Lee, Seoul (KR); Youngho Sohn, Seoul (KR); Mihyun Park, Seoul (KR); Jisoo Park, Seoul (KR); Hyunwoo Kim, Seoul (KR); Sungho Woo, Seoul (KR); Seonghyok Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days. days.

(21) Appl. No.: 15/169,620

(22) Filed: May 31, 2016

(65) Prior Publication Data

US 2017/0119307 A1 May 4, 2017

(30) Foreign Application Priority Data

Oct. 28, 2015 (KR) .......................... 10-2015-0150485

(51) Int. Cl.
*A61B 5/02* (2006.01)
*A61B 5/00* (2006.01)
(Continued)

(52) U.S. Cl.
CPC .............. *A61B 5/681* (2013.01); *A61B 5/002* (2013.01); *A61B 5/0013* (2013.01); *A61B 5/0022* (2013.01); *A61B 5/02108* (2013.01); *A61B 5/0402* (2013.01); *A61B 5/1172* (2013.01); *A61B 5/6844* (2013.01);
(Continued)

(58) Field of Classification Search
CPC ...... A61B 5/021; A61B 5/02416; A61B 5/681
See application file for complete search history.

(56) References Cited

U.S. PATENT DOCUMENTS

2002/0058876 A1* 5/2002 Chen ...................... A61B 5/021
600/485
2008/0249382 A1* 10/2008 Oh .......................... A61B 5/021
600/324
(Continued)

FOREIGN PATENT DOCUMENTS

KR 10-2015-0102592 9/2015

OTHER PUBLICATIONS

PCT International Application No. PCT/KR2016/007069, Notification of Transmittal of the International Search Report and the Written Opinion of the International Searching Authority, or Declaration with ISR and Written Opinion dated Oct. 26, 2016, 12 pages.

*Primary Examiner* — Michael D Abreu
(74) *Attorney, Agent, or Firm* — Lee, Hong, Degerman, Kang & Waimey

(57) ABSTRACT

A mobile terminal according to the present invention includes a terminal main body, a user input unit provided at the terminal main body and capable of receiving a control command for executing a specific function, a sensor unit provided adjacent to the user input unit and capable of sensing biometric information during the reception of the control command, and a controller capable of executing the specific function based on the control command and calculating a blood pressure value using the biometric information.

19 Claims, 26 Drawing Sheets

(51) Int. Cl.
  *A61B 5/021* (2006.01)
  *A61B 5/0402* (2006.01)
  *A61B 5/1172* (2016.01)
  *A61B 8/04* (2006.01)
  *G06F 3/01* (2006.01)
  *H04M 1/02* (2006.01)
  *H04M 1/725* (2006.01)
  *A61B 5/024* (2006.01)

(52) U.S. Cl.
  CPC .......... *A61B 5/6898* (2013.01); *A61B 5/7235* (2013.01); *A61B 5/7405* (2013.01); *A61B 5/746* (2013.01); *A61B 5/7435* (2013.01); *A61B 5/7455* (2013.01); *A61B 5/7475* (2013.01); *A61B 8/04* (2013.01); *G06F 3/017* (2013.01); *H04M 1/026* (2013.01); *H04M 1/7253* (2013.01); *A61B 5/02427* (2013.01); *A61B 2560/0214* (2013.01); *A61B 2560/0242* (2013.01)

(56) References Cited

U.S. PATENT DOCUMENTS

| | | |
|---|---|---|
| 2010/0225607 A1 | 9/2010 | Kim |
| 2011/0170750 A1 | 7/2011 | Kropp et al. |
| 2012/0029320 A1* | 2/2012 | Watson .............. A61B 5/02125 600/301 |
| 2014/0051941 A1 | 2/2014 | Messerschmidt |
| 2014/0135631 A1 | 5/2014 | Brumback et al. |
| 2017/0014036 A1* | 1/2017 | Kang .................. A61B 5/6825 |

\* cited by examiner

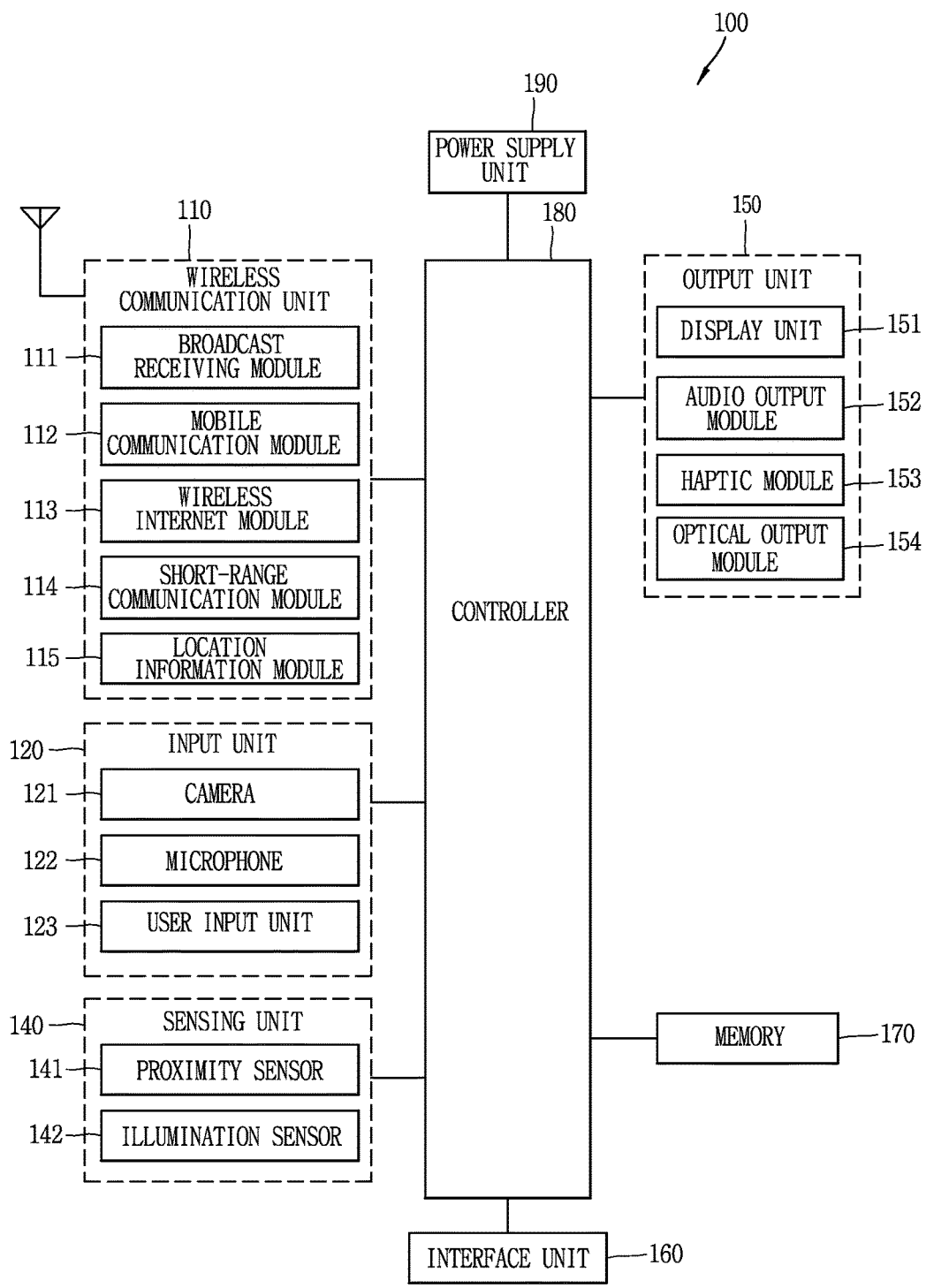

MOBILE TERMINAL AND METHOD OF CONTROLLING THE SAME

CROSS-REFERENCE TO RELATED APPLICATION

Pursuant to 35 U.S.C. § 119(a), this application claims the benefit of earlier filing date and right of priority to Korean Application No. 10-2015-0150485, filed on Oct. 28, 2015, the contents of which are all hereby incorporated by reference herein in its entirety.

BACKGROUND OF THE INVENTION

1. Field of the Invention

This specification relates to a mobile terminal capable of collecting user's biometric information.

2. Background of the Invention

Terminals may be divided into glass type terminals (mobile/portable terminals) and stationary terminals according to their mobility. Also, the glass type terminals may be classified into handheld terminals and vehicle mount terminals according to whether or not a user can directly carry.

As it becomes multifunctional, a mobile terminal can be allowed to capture still images or moving images, play music or video files, play games, receive broadcast and the like, so as to be implemented as an integrated multimedia player. Many efforts include not only changes and improvement of structural components implementing a mobile terminal but also software improvement to support and improve functions of the terminal.

In recent time, studies on various functions of collecting biometric information by use of sensors included in wearable-type terminals, which are wearable on a part of a user's body, are undergoing. However, when an additional sensing module is mounted to collect various biometric information, it may causes an increase in a weight of a terminal and inconvenience that the user has to consciously contact a part of his or her body with the sensing module.

SUMMARY OF THE INVENTION

Therefore, an aspect of the detailed description is to provide a mobile terminal capable of measuring blood pressure.

To achieve these and other advantages and in accordance with the purpose of this specification, as embodied and broadly described herein, there is provided a mobile terminal including a terminal main body, a user input unit provided at the terminal main body and capable of receiving a control command for executing a specific function, a sensor unit provided adjacent to the user input unit and capable of sensing biometric information during the reception of the control command, and a controller capable of executing the specific function based on the control command and calculating a blood pressure value using the biometric information.

In one exemplary embodiment disclosed herein, the controller may execute the specific function after the biometric information for measuring the blood pressure is collected. The mobile terminal may further include a display unit capable of outputting guide information for notifying the collection of the biometric information when the control command is received. Accordingly, a user can be provided with a blood pressure value based on the biometric information which is measured while the specific function is executed.

In one exemplary embodiment disclosed herein, the mobile terminal may further include a wireless communication unit capable of performing wireless communication with a wearable device, which is provided with a photo plethysmo gram (PPG) sensor and a first electrode unit. The controller may control the sensor unit to collect the biometric information when the wearable device transmits a wireless signal to notify a worn state of the wearable terminal. This may allow the user to obtain a blood pressure value which is measured in response to an external device executing the wireless communication being worn on the user's body.

In accordance with the present invention, the user can be provided with a blood pressure value using biometric information in response to a reception of a control command for executing a specific function. This may allow the user to collect the biometric information in a manner of applying the control command for executing the specific function, without any intentional measuring step for blood pressure measurement, which may result in obtaining blood pressure regularly measured under a preset specific environment.

Also, when a sensing module receives a control command for executing a specific function, biometric information can be collected at the same time of executing the specific function. The collected biometric information can also be stored together with results of the specific function.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from the detailed description.

BRIEF DESCRIPTION OF THE DRAWINGS

The accompanying drawings, which are included to provide a further understanding of the invention and are incorporated in and constitute a part of this specification, illustrate exemplary embodiments and together with the description serve to explain the principles of the invention.

In the drawings:

FIG. 1A is a block diagram of a mobile terminal in accordance with the present disclosure;

DETAILED DESCRIPTION OF THE INVENTION

Description will now be given in detail according to exemplary embodiments disclosed herein, with reference to the accompanying drawings. For the sake of brief description with reference to the drawings, the same or equivalent components may be provided with the same or similar reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In describing the present disclosure, moreover, the detailed description will be omitted when a specific description for publicly known technologies to which the invention pertains is judged to obscure the gist of the present disclosure. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

Mobile terminals presented herein may be implemented using a variety of different types of terminals. Examples of such terminals include cellular phones, smart phones, user equipment, laptop computers, digital broadcast terminals, personal digital assistants (PDAs), portable multimedia players (PMPs), navigators, slate PCs, tablet PCs, ultra books, wearable devices (for example, smart watches, smart glasses, head mounted displays (HMDs)), and the like.

By way of non-limiting example only, further description will be made with reference to particular types of mobile terminals. However, such teachings apply equally to other types of terminals, such as those types noted above. In addition, these teachings may also be applied to stationary terminals such as digital TV, desktop computers, digital signage, and the like.

Figure 1B:
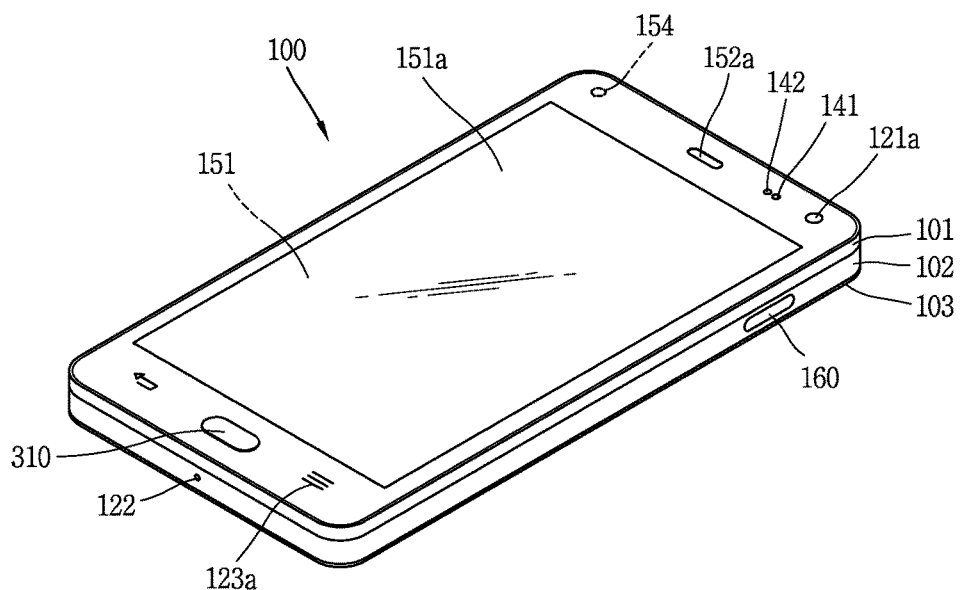
FIGS. 1B and 1C are conceptual views illustrating one example of the mobile terminal, viewed from different directions.
Figure 1C:
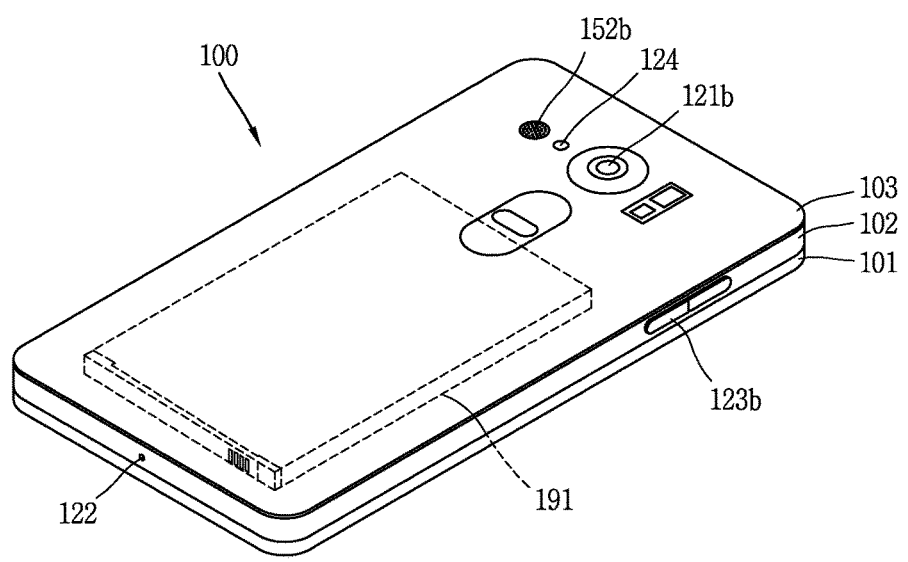

FIG. 1A is a block diagram of a mobile terminal in accordance with the present disclosure, and FIGS. 1B and 1C are conceptual views illustrating one example of the mobile terminal, viewed from different directions.

The mobile terminal 100 is shown having components such as a wireless communication unit 110, an input unit 120, a sensing unit 140, an output unit 150, an interface unit 160, a memory 170, a controller 180, and a power supply unit 190. It is understood that implementing all of the illustrated components is not a requirement, and that greater or fewer components may alternatively be implemented.

In more detail, the wireless communication unit 110 typically includes one or more modules which permit communications such as wireless communications between the mobile terminal 100 and a wireless communication system, communications between the mobile terminal 100 and another mobile terminal, communications between the mobile terminal 100 and an external server. Further, the wireless communication unit 110 typically includes one or more modules which connect the mobile terminal 100 to one or more networks.

The wireless communication unit 110 includes one or more of a broadcast receiving module 111, a mobile communication module 112, a wireless Internet module 113, a short-range communication module 114, and a location information module 115.

The input unit 120 includes a camera 121 or an image input unit for obtaining images or video, a microphone 122, which is one type of audio input device for inputting an audio signal, and a user input unit 123 (for example, a touch key, a mechanical key, and the like) for allowing a user to input information. Data (for example, audio, video, image, and the like) is obtained by the input unit 120 and may be analyzed and processed according to user commands.

The sensing unit 140 is typically implemented using one or more sensors configured to sense internal information of the mobile terminal, the surrounding environment of the mobile terminal, user information, and the like. For example, the sensing unit 140 may include at least one of a proximity sensor 141, an illumination sensor 142, a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 121), a microphone 122, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like). The mobile terminal disclosed herein may be configured to utilize information obtained from one or more sensors of the sensing unit 140, and combinations thereof.

The output unit 150 is typically configured to output various types of information, such as audio, video, tactile output, and the like. The output unit 150 is shown having at least one of a display unit 151, an audio output module 152, a haptic module 153, and an optical output module 154. The display unit 151 may have an inter-layered structure or an integrated structure with a touch sensor in order to facilitate a touch screen. The touch screen may provide an output interface between the mobile terminal 100 and a user, as well as function as the user input unit 123 which provides an input interface between the mobile terminal 100 and the user.

The interface unit 160 serves as an interface with various types of external devices that can be coupled to the mobile terminal 100. The interface unit 160, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the mobile terminal 100 may perform assorted control functions associated with a connected external device, in response to the external device being connected to the interface unit 160.

The memory 170 is typically implemented to store data to support various functions or features of the mobile terminal 100. For instance, the memory 170 may be configured to store application programs executed in the mobile terminal 100, data or instructions for operations of the mobile terminal 100, and the like. Some of these application programs may be downloaded from an external server via wireless communication. Other application programs may be installed within the mobile terminal 100 at time of manufacturing or shipping, which is typically the case for basic functions of the mobile terminal 100 (for example, receiving a call, placing a call, receiving a message, sending a message, and the like). It is common for application programs to be stored in the memory 170, installed in the mobile terminal 100, and executed by the controller 180 to perform an operation (or function) for the mobile terminal 100.

The controller 180 typically functions to control overall operation of the mobile terminal 100, in addition to the operations associated with the application programs. The controller 180 may provide or process information or functions appropriate for a user by processing signals, data, information and the like, which are input or output by the aforementioned various components, or activating application programs stored in the memory 170.

Also, the controller 180 controls some or all of the components illustrated in FIG. 1A according to the execution of an application program that have been stored in the memory 170. In addition, the controller 180 may control at least two of those components included in the mobile terminal to activate the application program.

The power supply unit 190 can be configured to receive external power or provide internal power in order to supply appropriate power required for operating elements and components included in the mobile terminal 100. The power supply unit 190 may include a battery, and the battery may be configured to be embedded in the terminal body, or configured to be detachable from the terminal body.

At least part of the components may cooperatively operate to implement an operation, a control or a control method of a mobile terminal according to various embodiments disclosed herein. Also, the operation, the control or the control method of the mobile terminal may be implemented on the mobile terminal by an activation of at least one application program stored in the memory 170.

Hereinafter, description will be given in more detail of the aforementioned components with reference to FIG. 1A, prior to describing various embodiments implemented through the mobile terminal 100.

First, regarding the wireless communication unit 110, the broadcast receiving module 111 is typically configured to receive a broadcast signal and/or broadcast associated information from an external broadcast managing entity via a broadcast channel. The broadcast channel may include a satellite channel, a terrestrial channel, or both. In some embodiments, two or more broadcast receiving modules 111 may be utilized to facilitate simultaneously receiving of two or more broadcast channels, or to support switching among broadcast channels.

The mobile communication module 112 can transmit and/or receive wireless signals to and from one or more network entities. Typical examples of a network entity include a base station, an external mobile terminal, a server, and the like. Such network entities form part of a mobile communication network, which is constructed according to technical standards or communication methods for mobile communications (for example, Global System for Mobile Communication (GSM), Code Division Multi Access (CDMA), CDMA2000 (Code Division Multi Access 2000), Enhanced Voice-Date Optimized or Enhanced Voice-Data Only (EV-DO), Wideband CDMA (WCDMA), High Speed Downlink Packet access (HSDPA), High Speed Uplink Packet Access (HSUPA), Long Term Evolution (LTE), LTE-advanced (LTE-A) and the like).

Examples of the wireless signals include audio call signals, video (telephony) call signals, or various formats of data to support communication of text and multimedia messages.

The wireless Internet module 113 is configured to facilitate wireless Internet access. This module may be internally or externally coupled to the mobile terminal 100. The wireless Internet module 113 may transmit and/or receive wireless signals via communication networks according to wireless Internet technologies.

Examples of such wireless Internet access include Wireless LAN (WLAN), Wireless Fidelity (Wi-Fi), Wi-Fi Direct, Digital Living Network Alliance (DLNA), Wireless Broadband (WiBro), Worldwide Interoperability for Microwave Access (WiMAX), High Speed Downlink Packet Access (HSDPA), High Speed Uplink Packet Access (HSUPA), Long Term Evolution (LTE), LTE-advanced (LTE-A) and the like. The wireless Internet module 113 may transmit/receive data according to one or more of such wireless Internet technologies, and other Internet technologies as well.

In some embodiments, when the wireless Internet access is implemented according to, for example, WiBro, HSDPA, HSUPA, GSM, CDMA, WCDMA, LTE, LET-A, and the like, as part of a mobile communication network, the wireless Internet module 113 may be understood as a type of the mobile communication module 112.

The short-range communication module 114 is configured to facilitate short-range communications. Suitable technologies for implementing such short-range communications include BLUETOOTH™, Radio Frequency IDentification (RFID), Infrared Data Association (IrDA), Ultra-WideBand (UWB), ZigBee, Near Field Communication (NFC), Wireless-Fidelity (Wi-Fi), Wi-Fi Direct, Wireless USB (Wireless Universal Serial Bus), and the like. The short-range communication module 114 in general supports wireless communications between the mobile terminal 100 and a wireless communication system, communications between the mobile terminal 100 and another mobile terminal 100, or communications between the mobile terminal and a network where another mobile terminal 100 (or an external server) is located, via wireless area networks. One example of the wireless area networks is a wireless personal area networks.

Here, another mobile terminal (which may be configured similarly to mobile terminal 100) may be a wearable device, for example, a smart watch, a smart glass or a head mounted display (HMD), which is able to exchange data with the mobile terminal 100 (or otherwise cooperate with the mobile terminal 100). The short-range communication module 114 may sense or recognize the wearable device, and permit communication between the wearable device and the mobile terminal 100. In addition, when the sensed wearable device is a device which is authenticated to communicate with the mobile terminal 100, the controller 180, for example, may cause transmission of at least part of data processed in the mobile terminal 100 to the wearable device via the short-range communication module 114. Hence, a user of the wearable device may use the data processed in the mobile terminal 100 on the wearable device. For example, when a call is received in the mobile terminal 100, the user may answer the call using the wearable device. Also, when a message is received in the mobile terminal 100, the user can check the received message using the wearable device.

The location information module 115 is generally configured to detect, calculate, derive or otherwise identify a position (or current position) of the mobile terminal. As an example, the location information module 115 includes a Global Position System (GPS) module, a Wi-Fi module, or both. For example, when the mobile terminal uses a GPS module, a position of the mobile terminal may be acquired using a signal sent from a GPS satellite. As another example, when the mobile terminal uses the Wi-Fi module, a position of the mobile terminal can be acquired based on information related to a wireless access point (AP) which transmits or receives a wireless signal to or from the Wi-Fi module. If desired, the location information module 115 may alternatively or additionally function with any of the other modules of the wireless communication unit 110 to obtain data related to the position of the mobile terminal. The location information module 115 is a module used for acquiring the position (or the current position) and may not be limited to a module for directly calculating or acquiring the position of the mobile terminal.

The input unit 120 may be configured to permit various types of inputs (information or signals) to the mobile terminal 100. Examples of such inputs include audio, image, video, data, and user input. Image and video input is often obtained using one or more cameras 121. Such cameras 121 may process image frames of still pictures or video obtained by image sensors in a video or image capture mode. The processed image frames can be displayed on the display unit 151 or stored in memory 170. Meanwhile, the cameras 121 may be arranged in a matrix configuration to permit a plurality of images having various angles or focal points to be input to the mobile terminal 100. Also, the cameras 121 may be located in a stereoscopic arrangement to acquire left and right images for implementing a stereoscopic image.

The microphone 122 processes an external audio signal into electric audio (sound) data. The processed audio data can be processed in various manners according to a function (or an application program) being executed in the mobile terminal 100. If desired, the microphone 122 may include assorted noise removing algorithms to remove unwanted noise generated in the course of receiving the external audio signal.

The user input unit 123 is a component that permits input by a user. Such user input may enable the controller 180 to control operation of the mobile terminal 100. The user input unit 123 may include one or more of a mechanical input element (for example, a mechanical key, a button located on a front and/or rear surface or a side surface of the mobile terminal 100, a dome switch, a jog wheel, a jog switch, and the like), or a touch-sensitive input element, among others. As one example, the touch-sensitive input element may be a virtual key, a soft key or a visual key, which is displayed on a touch screen through software processing, or a touch key which is located on the mobile terminal at a location that is other than the touch screen. On the other hand, the virtual key or the visual key may be displayed on the touch screen in various shapes, for example, graphic, text, icon, video, or a combination thereof.

The sensing unit 140 is generally configured to sense one or more of internal information of the mobile terminal, surrounding environment information of the mobile terminal, user information, or the like, and generate a corresponding sensing signal. The controller 180 generally cooperates with the sending unit 140 to control operation of the mobile terminal 100 or execute data processing, a function or an operation associated with an application program installed in the mobile terminal based on the sensing signal. The sensing unit 140 may be implemented using any of a variety of sensors, some of which will now be described in more detail.

The proximity sensor 141 refers to a sensor to sense presence or absence of an object approaching a surface, or an object located near a surface, by using an electromagnetic field, infrared rays, or the like without a mechanical contact. The proximity sensor 141 may be arranged at an inner region of the mobile terminal covered by the touch screen, or near the touch screen.

The proximity sensor 141, for example, may include any of a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and the like. When the touch screen is implemented as a capacitance type, the proximity sensor 141 can sense proximity of a pointer relative to the touch screen by changes of an electromagnetic field, which is responsive to an approach of an object with conductivity. In this case, the touch screen (touch sensor) may also be categorized as a proximity sensor.

The term "proximity touch" will often be referred to herein to denote the scenario in which a pointer is positioned to be proximate to the touch screen without contacting the touch screen. The term "contact touch" will often be referred to herein to denote the scenario in which a pointer makes physical contact with the touch screen. For the position corresponding to the proximity touch of the pointer relative to the touch screen, such position will correspond to a position where the pointer is perpendicular to the touch screen. The proximity sensor 141 may sense proximity touch, and proximity touch patterns (for example, distance, direction, speed, time, position, moving status, and the like). In general, controller 180 processes data corresponding to proximity touches and proximity touch patterns sensed by the proximity sensor 141, and cause output of visual information on the touch screen. In addition, the controller 180 can control the mobile terminal 100 to execute different operations or process different data (or information) according to whether a touch with respect to a point on the touch screen is either a proximity touch or a contact touch.

A touch sensor can sense a touch (or a touch input) applied to the touch screen, such as display unit 151, using any of a variety of touch methods. Examples of such touch methods include a resistive type, a capacitive type, an infrared type, and a magnetic field type, among others.

As one example, the touch sensor may be configured to convert changes of pressure applied to a specific part of the display unit 151, or convert capacitance occurring at a specific part of the display unit 151, into electric input signals. The touch sensor may also be configured to sense not only a touched position and a touched region, but also touch pressure and/or touch capacitance. A touch object is generally used to apply a touch input to the touch sensor. Examples of typical touch objects include a finger, a touch pen, a stylus pen, a pointer, or the like.

When a touch input is sensed by a touch sensor, corresponding signals may be transmitted to a touch controller. The touch controller may process the received signals, and then transmit corresponding data to the controller 180. Accordingly, the controller 180 may sense which region of the display unit 151 has been touched. Here, the touch controller may be a component separate from the controller 180, the controller 180, and combinations thereof.

Meanwhile, the controller 180 may execute the same or different controls according to a type of touch object that touches the touch screen or a touch key provided in addition to the touch screen. Whether to execute the same or different control according to the object which provides a touch input may be decided based on a current operating state of the mobile terminal 100 or a currently executed application program, for example.

The touch sensor and the proximity sensor may be implemented individually, or in combination, to sense various types of touches. Such touches includes a short (or tap) touch, a long touch, a multi-touch, a drag touch, a flick touch, a pinch-in touch, a pinch-out touch, a swipe touch, a hovering touch, and the like.

If desired, an ultrasonic sensor may be implemented to recognize position information relating to a touch object using ultrasonic waves. The controller 180, for example, may calculate a position of a wave generation source based on information sensed by an illumination sensor and a plurality of ultrasonic sensors. Since light is much faster than ultrasonic waves, the time for which the light reaches the optical sensor is much shorter than the time for which the ultrasonic wave reaches the ultrasonic sensor. The position of the wave generation source may be calculated using this fact. For instance, the position of the wave generation source may be calculated using the time difference from the time that the ultrasonic wave reaches the sensor based on the light as a reference signal.

The camera 121, which has been depicted as a component of the input unit 120, typically includes at least one a camera sensor (CCD, CMOS etc.), a photo sensor (or image sensors), and a laser sensor.

Implementing the camera 121 with a laser sensor may allow detection of a touch of a physical object with respect to a 3D stereoscopic image. The photo sensor may be laminated on, or overlapped with, the display device. The photo sensor may be configured to scan movement of the physical object in proximity to the touch screen. In more detail, the photo sensor may include photo diodes and transistors at rows and columns to scan content received at the photo sensor using an electrical signal which changes according to the quantity of applied light. Namely, the photo sensor may calculate the coordinates of the physical object according to variation of light to thus obtain position information of the physical object.

The display unit 151 is generally configured to output information processed in the mobile terminal 100. For example, the display unit 151 may display execution screen information of an application program executing at the mobile terminal 100 or user interface (UI) and graphic user interface (GUI) information in response to the execution screen information.

Also, the display unit 151 may be implemented as a stereoscopic display unit for displaying stereoscopic images.

A typical stereoscopic display unit may employ a stereoscopic display scheme such as a stereoscopic scheme (a glass scheme), an auto-stereoscopic scheme (glassless scheme), a projection scheme (holographic scheme), or the like.

The audio output module 152 is generally configured to output audio data. Such audio data may be obtained from any of a number of different sources, such that the audio data may be received from the wireless communication unit 110 or may have been stored in the memory 170. The audio data may be output during modes such as a signal reception mode, a call mode, a record mode, a voice recognition mode, a broadcast reception mode, and the like. The audio output module 152 can provide audible output related to a particular function (e.g., a call signal reception sound, a message reception sound, etc.) performed by the mobile terminal 100. The audio output module 152 may also be implemented as a receiver, a speaker, a buzzer, or the like.

A haptic module 153 can be configured to generate various tactile effects that a user feels, perceive, or otherwise experience. A typical example of a tactile effect generated by the haptic module 153 is vibration. The strength, pattern and the like of the vibration generated by the haptic module 153 can be controlled by user selection or setting by the controller. For example, the haptic module 153 may output different vibrations in a combining manner or a sequential manner.

Besides vibration, the haptic module 153 can generate various other tactile effects, including an effect by stimulation such as a pin arrangement vertically moving to contact skin, a spray force or suction force of air through a jet orifice or a suction opening, a touch to the skin, a contact of an electrode, electrostatic force, an effect by reproducing the sense of cold and warmth using an element that can absorb or generate heat, and the like.

The haptic module 153 can also be implemented to allow the user to feel a tactile effect through a muscle sensation such as the user's fingers or arm, as well as transferring the tactile effect through direct contact. Two or more haptic modules 153 may be provided according to the particular configuration of the mobile terminal 100.

An optical output module 154 can output a signal for indicating an event generation using light of a light source. Examples of events generated in the mobile terminal 100 may include message reception, call signal reception, a missed call, an alarm, a schedule alarm, an email reception, information reception through an application, and the like.

A signal output by the optical output module 154 may be implemented in such a manner that the mobile terminal emits monochromatic light or light with a plurality of colors. The signal output may be terminated as the mobile terminal senses that a user has checked the generated event, for example.

The interface unit 160 serves as an interface for external devices to be connected with the mobile terminal 100. For example, the interface unit 160 can receive data transmitted from an external device, receive power to transfer to elements and components within the mobile terminal 100, or transmit internal data of the mobile terminal 100 to such external device. The interface unit 160 may include wired or wireless headset ports, external power supply ports, wired or wireless data ports, memory card ports, ports for connecting a device having an identification module, audio input/output (I/O) ports, video I/O ports, earphone ports, or the like.

The identification module may be a chip that stores various information for authenticating authority of using the mobile terminal 100 and may include a user identity module (UIM), a subscriber identity module (SIM), a universal subscriber identity module (USIM), and the like. In addition, the device having the identification module (also referred to herein as an "identifying device") may take the form of a smart card. Accordingly, the identifying device can be connected with the terminal 100 via the interface unit 160.

When the mobile terminal 100 is connected with an external cradle, the interface unit 160 can serve as a passage to allow power from the cradle to be supplied to the mobile terminal 100 or may serve as a passage to allow various command signals input by the user from the cradle to be transferred to the mobile terminal there through. Various command signals or power input from the cradle may operate as signals for recognizing that the mobile terminal is properly mounted on the cradle.

The memory 170 can store programs to support operations of the controller 180 and store input/output data (for example, phonebook, messages, still images, videos, etc.). The memory 170 may store data related to various patterns of vibrations and audio which are output in response to touch inputs on the touch screen.

The memory 170 may include one or more types of storage mediums including a flash memory type, a hard disk type, a solid state disk (SSD) type, a silicon disk drive (SDD) type, a multimedia card micro type, a card-type memory (e.g., SD or DX memory, etc), a Random Access Memory (RAM), a Static Random Access Memory (SRAM), a Read-Only Memory (ROM), an Electrically Erasable Programmable Read-Only Memory (EEPROM), a Programmable Read-Only memory (PROM), a magnetic memory, a magnetic disk, an optical disk, and the like. The mobile terminal 100 may also be operated in relation to a network storage device that performs the storage function of the memory 170 over a network, such as the Internet.

The controller 180 may typically control the general operations of the mobile terminal 100. For example, the controller 180 may set or release a lock state for restricting a user from inputting a control command with respect to applications when a status of the mobile terminal meets a preset condition.

The controller 180 can also perform the controlling and processing associated with voice calls, data communications, video calls, and the like, or perform pattern recognition processing to recognize a handwriting input or a picture drawing input performed on the touch screen as characters or images, respectively. In addition, the controller 180 can control one or a combination of those components in order to implement various exemplary embodiments disclosed herein.

The power supply unit 190 receives external power or provide internal power and supply the appropriate power required for operating respective elements and components included in the mobile terminal 100. The power supply unit 190 may include a battery, which is typically rechargeable or be detachably coupled to the terminal body for charging.

The power supply unit 190 may include a connection port. The connection port may be configured as one example of the interface unit 160 to which an external charger for supplying power to recharge the battery is electrically connected.

As another example, the power supply unit 190 may be configured to recharge the battery in a wireless manner without use of the connection port. In this example, the power supply unit 190 can receive power, transferred from an external wireless power transmitter, using at least one of an inductive coupling method which is based on magnetic induction or a magnetic resonance coupling method which is based on electromagnetic resonance.

Various embodiments described herein may be implemented in a computer-readable medium, a machine-readable medium, or similar medium using, for example, software, hardware, or any combination thereof.

Referring now to FIGS. 1B and 1C, the mobile terminal 100 is described with reference to a bar-type terminal body. However, the mobile terminal 100 may alternatively be implemented in any of a variety of different configurations. Examples of such configurations include watch-type, clip-type, glasses-type, or as a folder-type, flip-type, slide-type, swing-type, and swivel-type in which two and more bodies are combined with each other in a relatively movable manner, and combinations thereof. Discussion herein will often relate to a particular type of mobile terminal. However, such teachings with regard to a particular type of mobile terminal will generally apply to other types of mobile terminals as well.

Here, considering the mobile terminal 100 as at least one assembly, the terminal body may be understood as a conception referring to the assembly.

The mobile terminal 100 will generally include a case (for example, frame, housing, cover, and the like) forming the appearance of the terminal. In this embodiment, the case is formed using a front case 101 and a rear case 102. Various electronic components are incorporated into a space formed between the front case 101 and the rear case 102. At least one middle case may be additionally positioned between the front case 101 and the rear case 102.

The display unit 151 is shown located on the front side of the terminal body to output information. As illustrated, a window 151a of the display unit 151 may be mounted to the front case 101 to form the front surface of the terminal body together with the front case 101.

In some embodiments, electronic components may also be mounted to the rear case 102. Examples of such electronic components include a detachable battery 191, an identification module, a memory card, and the like. Rear cover 103 is shown covering the electronic components, and this cover may be detachably coupled to the rear case 102. Therefore, when the rear cover 103 is detached from the rear case 102, the electronic components mounted to the rear case 102 are externally exposed.

As illustrated, when the rear cover 103 is coupled to the rear case 102, a side surface of the rear case 102 is partially exposed. In some cases, upon the coupling, the rear case 102 may also be completely shielded by the rear cover 103. In some embodiments, the rear cover 103 may include an opening for externally exposing a camera 121b or an audio output module 152b.

The cases 101, 102, 103 may be formed by injection-molding synthetic resin or may be formed of a metal, for example, stainless steel (STS), aluminum (Al), titanium (Ti), or the like.

As an alternative to the example in which the plurality of cases form an inner space for accommodating components, the mobile terminal 100 may be configured such that one case forms the inner space. In this example, a mobile terminal 100 having a uni-body is formed in such a manner that synthetic resin or metal extends from a side surface to a rear surface.

If desired, the mobile terminal 100 may include a waterproofing unit (not shown) for preventing introduction of water into the terminal body. For example, the waterproofing unit may include a waterproofing member which is located between the window 151a and the front case 101, between the front case 101 and the rear case 102, or between the rear case 102 and the rear cover 103, to hermetically seal an inner space when those cases are coupled.

The mobile terminal 100 may include a display unit 151, first and second audio output module 152a and 152b, a proximity sensor 141, an illumination sensor 142, an optical output module 154, first and second cameras 121a and 121b, first and second manipulation units 123a and 123b, a microphone 122, an interface unit 160, and the like.

Hereinafter, as illustrated in FIGS. 1B and 1C, description will be given of the exemplary mobile terminal 100 in which the front surface of the terminal body is shown having the display unit 151, the first audio output module 152a, the proximity sensor 141, the illumination sensor 142, the optical output module 154, the first camera 121a, and the first manipulation unit 123a, the side surface of the terminal body is shown having the second manipulation unit 123b, the microphone 122, and the interface unit 160, and the rear surface of the terminal body is shown having the second audio output module 152b and the second camera 121b.

However, those components may not be limited to the arrangement. Some components may be omitted or rearranged or located on different surfaces. For example, the first manipulation unit 123a may be located on another surface of the terminal body, and the second audio output module 152b may be located on the side surface of the terminal body other than the rear surface of the terminal body.

The display unit 151 outputs information processed in the mobile terminal 100. For example, the display unit 151 may display execution screen information of an application program executing at the mobile terminal 100 or user interface (UI) and graphic user interface (GUI) information in response to the execution screen information.

The display unit 151 may be implemented using one or more suitable display devices. Examples of such suitable display devices include a liquid crystal display (LCD), a thin film transistor-liquid crystal display (TFT-LCD), an organic light emitting diode (OLED), a flexible display, a 3-dimensional (3D) display, an e-ink display, and combinations thereof.

The display unit 151 may be implemented using two display devices, which can implement the same or different display technology. For instance, a plurality of the display units 151 may be arranged on one side, either spaced apart from each other, or these devices may be integrated, or these devices may be arranged on different surfaces.

The display unit 151 may also include a touch sensor which senses a touch input received at the display unit. When a touch is input to the display unit 151, the touch sensor may be configured to sense this touch and the controller 180, for example, may generate a control command or other signal corresponding to the touch. The content which is input in the touching manner may be a text or numerical value, or a menu item which can be indicated or designated in various modes.

The touch sensor may be configured in a form of a film having a touch pattern, disposed between the window 151a and a display on a rear surface of the window 151a, or a metal wire which is patterned directly on the rear surface of the window 151a. Alternatively, the touch sensor may be integrally formed with the display. For example, the touch sensor may be disposed on a substrate of the display or within the display.

The display unit 151 may also form a touch screen together with the touch sensor. Here, the touch screen may serve as the user input unit 123 (see FIG. 1A). Therefore, the touch screen may replace at least some of the functions of the first manipulation unit 123a.

The first audio output module 152a may be implemented in the form of a receiver for transferring call sounds to a user's ear and the second audio output module 152b may be implemented in the form of a loud speaker to output alarm sounds, multimedia audio reproduction, and the like.

The window 151a of the display unit 151 will typically include an aperture to permit audio generated by the first audio output module 152a to pass. One alternative is to allow audio to be released along an assembly gap between the structural bodies (for example, a gap between the window 151a and the front case 101). In this case, a hole independently formed to output audio sounds may not be seen or is otherwise hidden in terms of appearance, thereby further simplifying the appearance and manufacturing of the mobile terminal 100.

The optical output module 154 can be configured to output light for indicating an event generation. Examples of such events include a message reception, a call signal reception, a missed call, an alarm, a schedule alarm, an email reception, information reception through an application, and the like. When a user has checked a generated event, the controller 180 can control the optical output module 154 to stop the light output.

The first camera 121a can process image frames such as still or moving images obtained by the image sensor in a capture mode or a video call mode. The processed image frames can then be displayed on the display unit 151 or stored in the memory 170.

The first and second manipulation units 123a and 123b are examples of the user input unit 123, which may be manipulated by a user to provide input to the mobile terminal 100. The first and second manipulation units 123a and 123b may also be commonly referred to as a manipulating portion, and may employ any tactile method that allows the user to perform manipulation such as touch, push, scroll, or the like. The first and second manipulation units 123a and 123b may also employ any non-tactile method that allows the user to perform manipulation such as proximity touch, hovering, or the like.

FIG. 1B illustrates the first manipulation unit 123a as a touch key, but possible alternatives include a mechanical key, a push key, a touch key, and combinations thereof.

Input received at the first and second manipulation units 123a and 123b may be used in various ways. For example, the first manipulation unit 123a may be used by the user to provide an input to a menu, home key, cancel, search, or the like, and the second manipulation unit 123b may be used by the user to provide an input to control a volume level being output from the first or second audio output modules 152a or 152b, to switch to a touch recognition mode of the display unit 151, or the like.

As another example of the user input unit 123, a rear input unit (not shown) may be located on the rear surface of the terminal body. The rear input unit can be manipulated by a user to provide input to the mobile terminal 100. The input may be used in a variety of different ways. For example, the rear input unit may be used by the user to provide an input for power on/off, start, end, scroll, control volume level being output from the first or second audio output modules 152a or 152b, switch to a touch recognition mode of the display unit 151, and the like. The rear input unit may be configured to permit touch input, a push input, or combinations thereof.

The rear input unit may be located to overlap the display unit 151 of the front side in a thickness direction of the terminal body. As one example, the rear input unit may be located on an upper end portion of the rear side of the terminal body such that a user can easily manipulate it using a forefinger when the user grabs the terminal body with one hand. Alternatively, the rear input unit can be positioned at most any location of the rear side of the terminal body.

When the rear input unit is provided on the rear surface of the terminal body, new types of user interfaces using the rear input unit can be implemented. Embodiments that include the aforementioned touch screen or the rear input unit may implement some or all of the functionality of the first manipulation unit 123a provided on the front surface of the terminal body. As such, in situations where the first manipulation unit 123a is omitted from the front side, the display unit 151 can have a larger screen.

As a further alternative, the mobile terminal 100 may include a finger scan sensor which scans a user's fingerprint. The controller 180 can then use fingerprint information sensed by the finger scan sensor as part of an authentication procedure. The finger scan sensor may also be installed in the display unit 151 or implemented in the user input unit 123.

The microphone 122 is shown located at an end of the mobile terminal 100, but other locations are possible. If desired, multiple microphones may be implemented, with such an arrangement permitting the receiving of stereo sounds.

The interface unit 160 may serve as a path allowing the mobile terminal 100 to interface with external devices. For example, the interface unit 160 may include one or more of a connection terminal for connecting to another device (for example, an earphone, an external speaker, or the like), a port for near field communication (for example, an Infrared Data Association (IrDA) port, a Bluetooth port, a wireless LAN port, and the like), or a power supply terminal for supplying power to the mobile terminal 100. The interface unit 160 may be implemented in the form of a socket for accommodating an external card, such as Subscriber Identification Module (SIM), User Identity Module (UIM), or a memory card for information storage.

The second camera 121b is shown located at the rear side of the terminal body and includes an image capturing direction that is substantially opposite to the image capturing direction of the first camera unit 121a.

The second camera 121b can include a plurality of lenses arranged along at least one line. The plurality of lenses may also be arranged in a matrix configuration. The cameras may be referred to as an "array camera." When the second camera 121b is implemented as an array camera, images may be captured in various manners using the plurality of lenses and images with better qualities.

A flash 124 is shown adjacent to the second camera 121b. When an image of a subject is captured with the camera 121b, the flash 124 may illuminate the subject.

The second audio output module 152b can be located on the terminal body. The second audio output module 152b may implement stereophonic sound functions in conjunction with the first audio output module 152a, and may be also used for implementing a speaker phone mode for call communication.

At least one antenna for wireless communication may be located on the terminal body. The antenna may be installed in the terminal body or formed by the case. For example, an antenna which configures a part of the broadcast receiving module 111 may be retractable into the terminal body. Alternatively, an antenna may be formed using a film attached to an inner surface of the rear cover 103, or a case that includes a conductive material.

A power supply unit 190 for supplying power to the mobile terminal 100 may include a battery 191, which is mounted in the terminal body or detachably coupled to an outside of the terminal body.

The battery 191 may receive power via a power source cable connected to the interface unit 160. Also, the battery 191 can be recharged in a wireless manner using a wireless charger. Wireless charging may be implemented by magnetic induction or electromagnetic resonance.

The rear cover 103 is shown coupled to the rear case 102 for shielding the battery 191, to prevent separation of the battery 191, and to protect the battery 191 from an external impact or from foreign material. When the battery 191 is detachable from the terminal body, the rear case 103 may be detachably coupled to the rear case 102.

An accessory for protecting an appearance or assisting or extending the functions of the mobile terminal 100 can also be provided on the mobile terminal 100. As one example of an accessory, a cover or pouch for covering or accommodating at least one surface of the mobile terminal 100 may be provided. The cover or pouch may cooperate with the display unit 151 to extend the function of the mobile terminal 100. Another example of the accessory is a touch pen for assisting or extending a touch input to a touch screen.

The mobile terminal disclosed herein may collect biometric information related to a user in a manner of being brought into contact with a part of the user's body. The mobile terminal according to one exemplary embodiment disclosed herein may measure blood pressure using at least one of the collected biometric information. Hereinafter, a structure of the mobile terminal which is configured to measure the blood pressure will be described in detail.

Figure 2A:
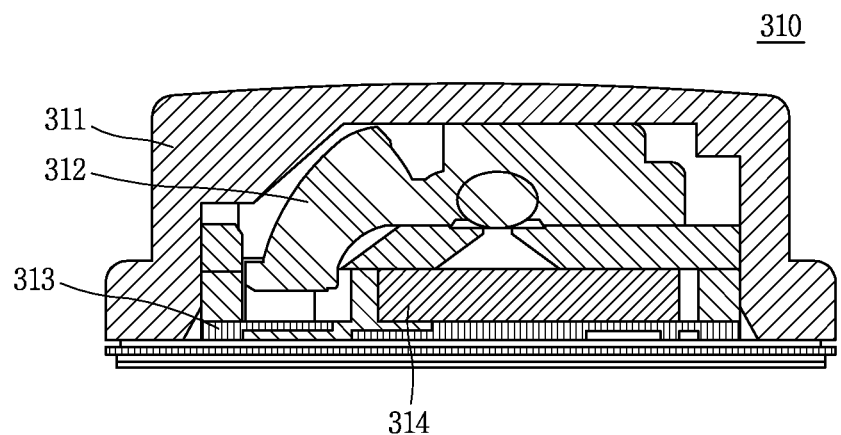
FIG. 2A is a sectional view illustrating a structure of a sensor unit which is capable of collecting biometric information.
Figure 2B:
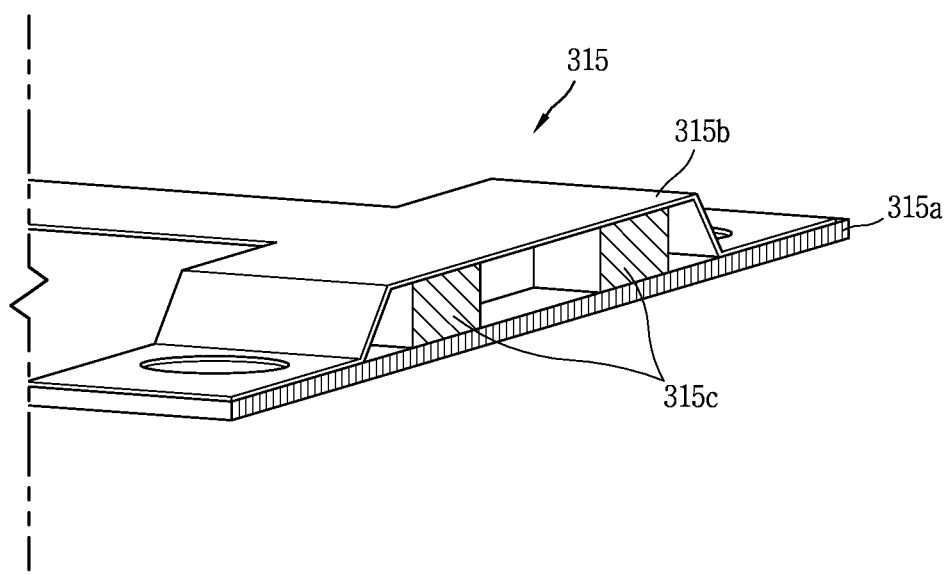
FIG. 2B is a conceptual view of a pressure sensor.

FIG. 2A is a sectional view illustrating a structure of a sensor unit which is capable of collecting biometric information, FIG. 2B is a conceptual view of a pressure sensor.

As illustrated in FIGS. 1B and 2A, a sensing module 310 may be configured integrally with the signal input unit that generates a control command. The mobile terminal disclosed herein may measure blood pressure using pulse wave information which is sensed during reception of an external force. That is, the mobile terminal may measure blood pressure using sensed pressure and pulse wave information.

For example, the sensing module 310 may be provided at a front surface of the mobile terminal 100, and implemented as a button which generates a control signal in a pressing manner. Although not illustrated in detail, the sensing module 310 may include components, such as an actuator that voltage value differs depending on pressure applied thereto, and the like.

The sensing module 310 may include a cover unit 311, an optical lens unit 312, a light-emitting unit 313, a light-receiving unit 314 and a pressure sensor 315. The cover unit 311 may define appearance of the sensing module 310 and come in contact with a part of a user's body. The cover unit 311 may accommodate therein the optical lens unit 312, the light-emitting unit 313, the light-receiving unit 314 and the pressure sensor 315. The cover unit 311 may be moved (transformed, pushed down, etc.) in a thickness direction of the mobile terminal 100 by an external force. The cover unit 311 may include an elastic member which is elastically moved by an external force and restored to its original state.

The cover unit 311 may also include an open area or a light-transmissive area through which light emitted from the light-emitting unit 313 is transferred to the user's body. The light-emitting unit 313 may be implemented as an infrared (IR) light emitting diode (LED). The optical lens unit 312 may be disposed above the light-emitting unit 313. The optical lens unit 312 may reflect light emitted from the light-emitting unit 313 to be concentrated on one area of the cover unit 311. Here, the one area may correspond to the open area or the light-transmissive area of the cover unit 311. Also, the optical lens unit 312 may be configured such that incoming light which is emitted from the light-emitting unit 313 and reflected by the body brought into contact with the cover unit 311 can be transferred to the light-receiving unit 314.

The light-receiving unit 314 may sense light of the IR LED reflected by a finger. The light-receiving unit 314 may have an array structure. In this instance, the light-receiving unit 314 may sense a movement (or a motion) of the finger on the cover unit 311 based on the light reflected by the finger.

The pressure sensor 315 may be disposed within the cover unit 311 to sense an external force applied to the cover unit 311. The pressure sensor 315 may support the cover unit 311, and at least one of the optical lens unit 312, the light-emitting unit 313 and the light-receiving unit 314, so as to sense an external force.

Referring to FIG. 2B, the pressure sensor 315 may be provided with a supporting portion 315a, a sensing portion 315b, and an elastic portion 315c interposed between the sensing portion 315b and the supporting portion 315a. The pressure sensor 315 may be configured to be transformable by an external force, and sense pressure using a voltage value which changes due to the transformation.

Meanwhile, the sensing module 310 may further include a leaf spring that supports the cover unit 311 affected by an external force. The pressure sensor 315 may be disposed to face the leaf spring, and have a pressing structure that it is pressed by the external force.

The mobile terminal disclosed herein may be provided with a photo plethysmo gram (PPG) sensor and a pressure sensor in the signal input unit that is configured for a user to generate a control signal by pressing it. This structure may allow for collecting information for measuring (calculating) blood pressure, without use of an additional space. Also, such sensors, namely, the PPG sensor and the pressure sensor, may be formed integrally with the signal input unit, so as to collect biometric information for measuring blood pressure while a specific function is executed.

Figure 3:
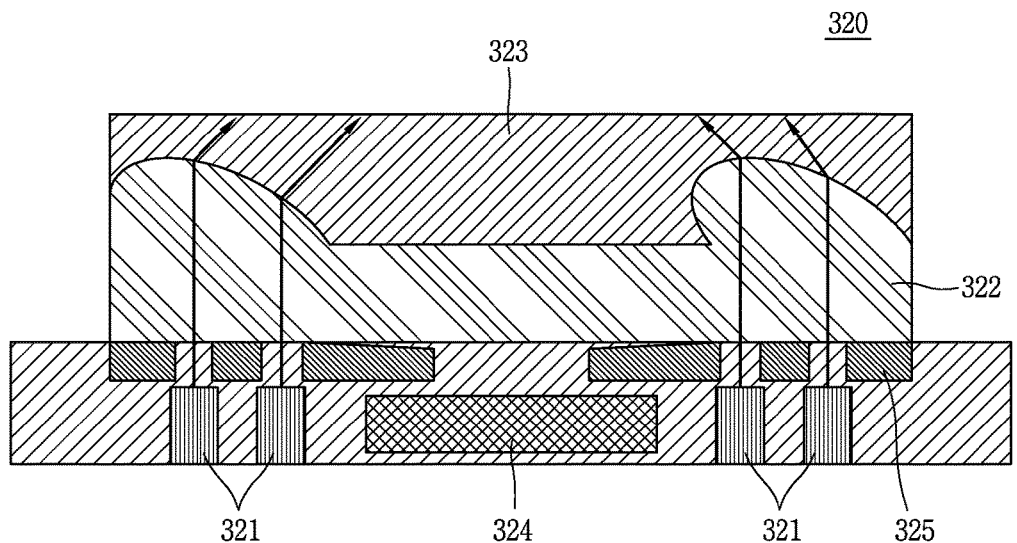
FIG. 3 is a conceptual view illustrating a sensing module in accordance with one exemplary embodiment.

FIG. 3 is a conceptual view illustrating a sensing module in accordance with one exemplary embodiment. A mobile terminal according to this exemplary embodiment may calculate blood pressure using pressure and pulse wave information.

A sensing module 320 according to FIG. 3 may be configured to detect pulse waves, a fingerprint, pressure and the like, and the controller 180 may measure blood pressure using the detected pulse waves and pressure. The sensing module 320 may include a plurality of light-emitting units 321, an optical lens unit 322, a cover unit 323, a light-receiving unit 324, and a matrix layer 325. The light-emitting units 321 may be implemented as LEDs.

Light that is emitted from the light-emitting units 321 and passes through the matrix layer 325 may flow through the optical lens unit 322 and be reflected by a finger that is brought into contact with the cover unit 323.

The sensing module 320 disclosed in this exemplary embodiment may sense (detect) a movement (or a motion) of a finger by the plurality of light-emitting units 321 and the matrix layer 325. The controller 180 may generate a control command in response to the detected movement of the finger.

The controller 180 may detect pulse waves using light, which is reflected by the finger coming in contact with the sensing module 320, by use of the plurality of light-emitting units 321 and the light-receiving unit 324. Although not illustrated in detail, the sensing module 320 may include a pressure sensor. Here, the pressure sensor may be substantially the same as the pressure sensor of FIG. 2B. The controller 180 may measure blood pressure based on the measured pulse wave and pressure.

Figure 4:
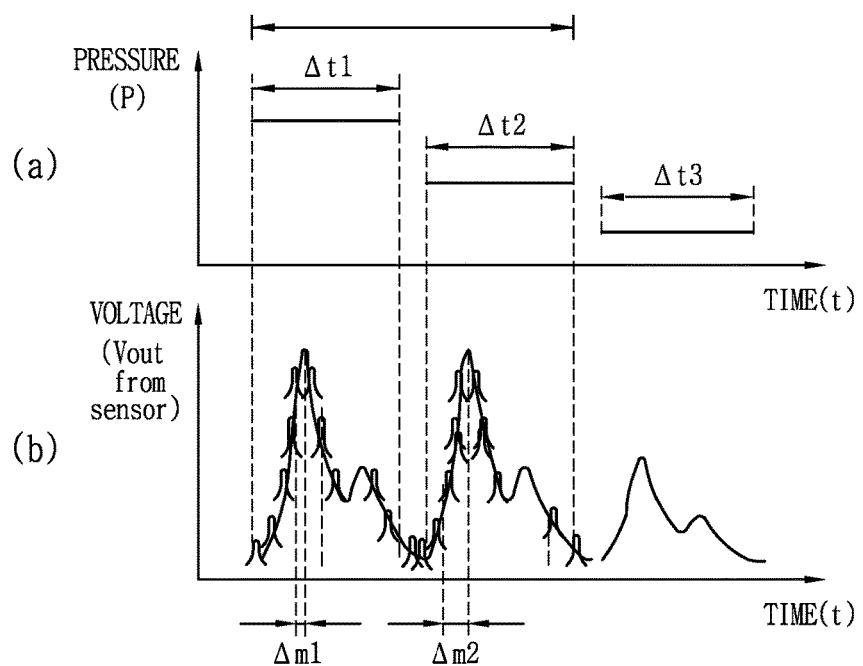
FIG. 4 is a view illustrating pulse waves measured while pressure is applied.

FIG. 4 is a view illustrating pulse waves measured while pressure is applied.

(a) of FIG. 4 illustrates pressure applied according to a lapse of time, and (b) of FIG. 4 illustrates pulse waves detected by a photo plethysmo gram (PPG) sensor in the form of a waveform corresponding to changes of voltages according to a lapse of time.

The light-emitting unit 313 and the light-receiving unit 314 may configure a PPG sensor. The PPG sensor may detect a signal indicating a pulsation element generated by a heartbeat, on the basis of a signal which is obtained in a manner of emitting light of a specific wavelength band to a user's body and detecting reflected or transmitted light of the emitted light. When light is emitted from the light-emitting unit 313 to the user's body, some light may be absorbed by blood, bones and tissues, and some light may be transmitted to reach the light-receiving unit 314. An amount of light absorbed is proportional to an amount of skin, tissues and blood located on a path that the light passes, and is not changed except for a change in blood flow due to heartbeats. Therefore, the change in the amount of light absorbed may be proportional to the change in the blood flow. Since the transmitted light detected in the light-receiving unit 314 is received by being subtracted by an amount of light absorbed by a finger, a change in an amount of the transmitted light may reflect the change in the blood flow. Therefore, a change in an amount of blood which is synchronized with the heartbeats can be detected by measuring an amount of light received in the light-receiving unit 314.

The controller 180 may estimate blood pressure of portions to be examined based on time differences between time points corresponding to peaks of detected pulse waves and time points corresponding to peaks of filtered pulse waves. Then, the highest blood pressure of the estimated blood pressure may be estimated as systolic blood pressure (BP) and the lowest blood pressure may be estimated as diastolic BR However, the present invention may not be limited to this, and other blood pressure, such as mean blood pressure, may also be estimated using the estimated blood pressure.

Figure 5A:
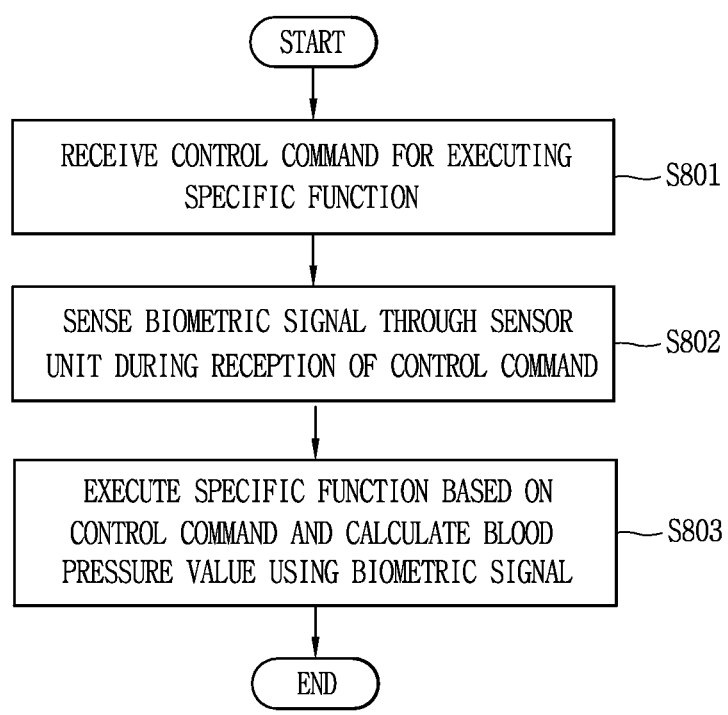
FIG. 5A is a flowchart illustrating a method for controlling a mobile terminal in accordance with one exemplary embodiment.
Figure 5B:
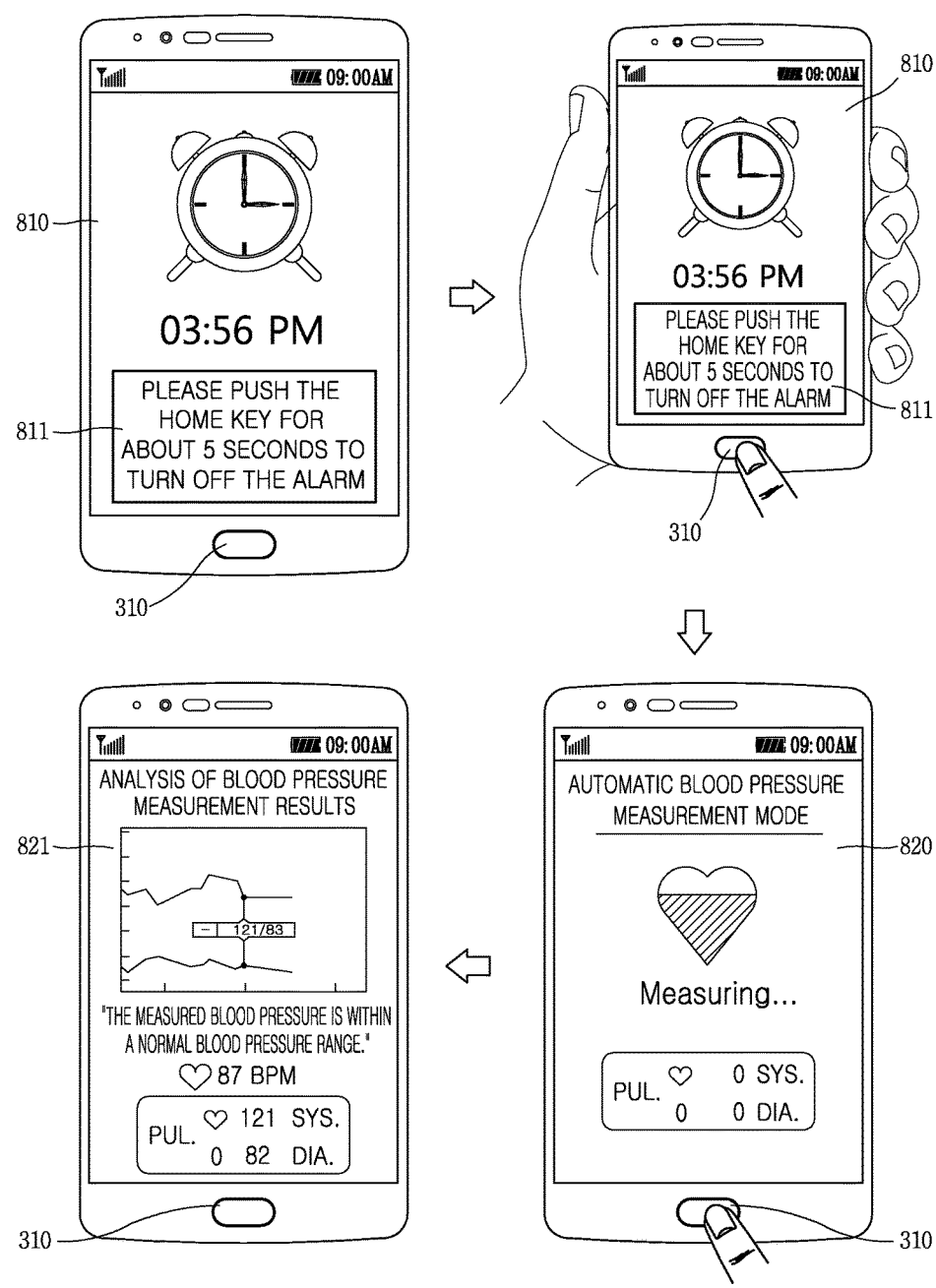
FIGS. 5B and 5C are conceptual views illustrating the control method of FIG. 5A.
Figure 5C:
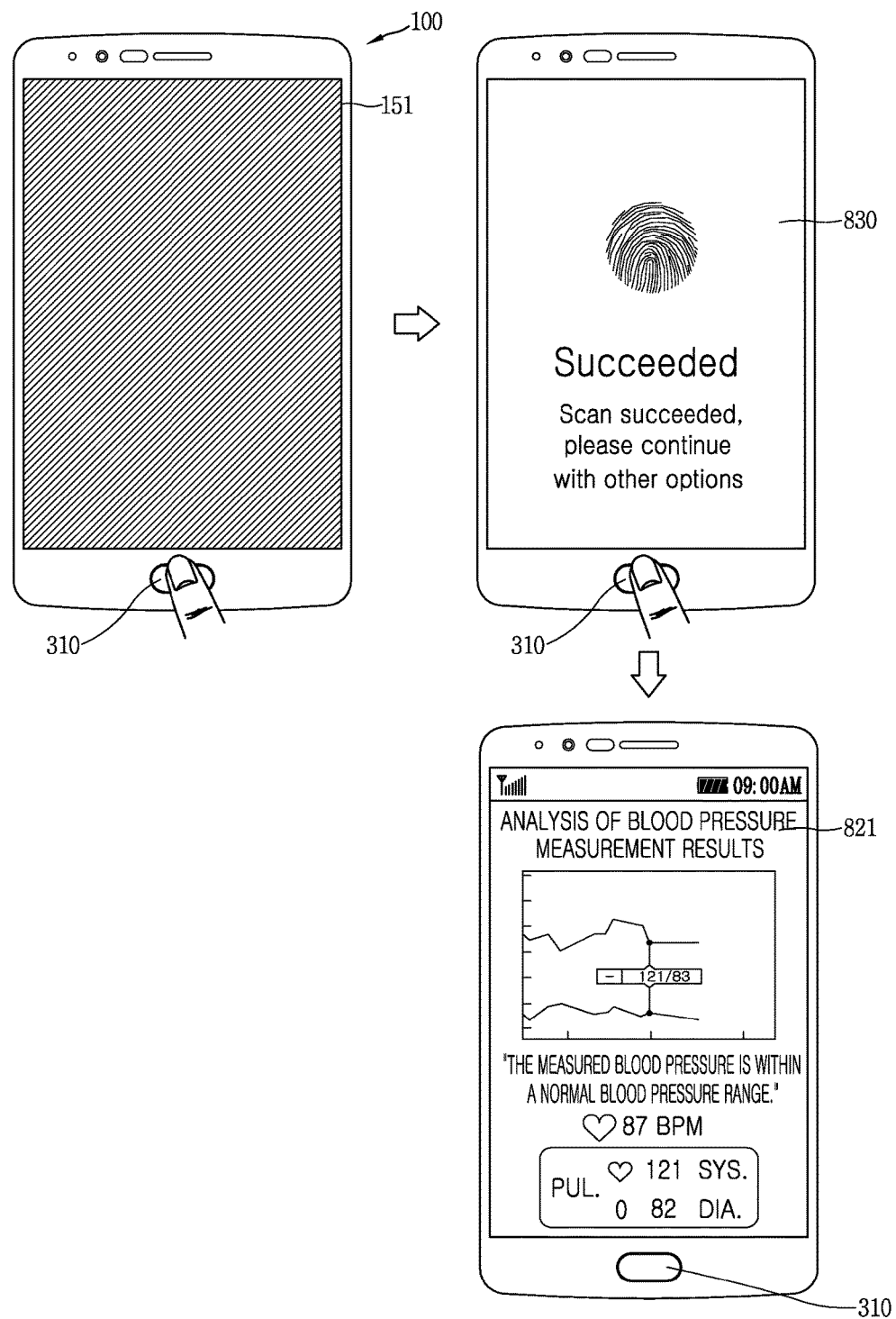

FIG. 5A is a flowchart illustrating a method for controlling a mobile terminal in accordance with one exemplary embodiment, and FIGS. 5B and 5C are conceptual views illustrating the control method of FIG. 5A.

Upon receiving a control command for performing a specific function (S801), the mobile terminal according to this exemplary embodiment may detect a biometric signal through a sensor unit during the reception of the control command (S802). The controller may execute the specific function based on the control command, and calculate a blood pressure value using the biometric signal (S803).

FIG. 5B illustrates one example in which the specific function is to prevent an output of an alarm. The output unit of the mobile terminal 100 may output alarm information according to a user's setting or in response to a specific control signal. The alarm information may include at least one of an alarm screen 810 output on the display unit 151, an alarm sound output through the audio output module 152, and an alarm vibration output through the haptic module 153.

The controller 180 may control at least one of the display unit 151, the audio output module 152 and the haptic module 153 to prevent the output of the alarm information, in response to a control command applied to the sensing module 310.

The display unit 151 may output guide information 811 for collecting the biometric information, during the output of the alarm information. The guide information may be configured in the form of text indicating the user to press a home key (the sensing module 310), as illustrated in the drawing, but the present invention may not be limited to this. For example, the guide information may be visual information or voice information.

The guide information 811 may be output at the same time point of executing the specific function associated with the control command (i.e., the time point of outputting the alarm information), or after receiving the control command. Or, the execution of the specific function may be delayed until biometric information for calculating the blood pressure value is collected.

The user may set biometric information to be collected at a time point that morning alarm information is output, or set the alarm information to be output at a specific time when a blood pressure value is required.

As illustrated in FIGS. 2A, 2B and 5B, the controller 180 may prevent the output of the alarm information and control the light-emitting unit 313, the light-receiving unit 314 and the pressure sensor 315, in response to the control command.

In detail, when a control signal is generated in a manner of pressing the sensing module 310 configured as a button, the controller 180 may control the light-emitting unit 313 to emit light. Or, the controller 180 may activate the light-emitting unit 313 and the light-receiving unit 314 when an external force stronger than a reference force (or pressure) is sensed for a preset period of time by the pressure sensor 315. Or, the controller 180 may activate the sensing module 310 to collect biometric information when the alarm information is output.

The controller 180 may measure a blood pressure value based on pulse wave information according to an amount of light detected by the light-receiving unit 314, and pressure sensed by the pressure sensor 315.

The controller 180 may continuously output the alarm information while the biometric information is collected enough to calculate the blood pressure value. When the blood pressure value is calculated, the controller 180 may start to prevent the output of the alarm information based on the control command.

However, prior to acquiring the pulse wave information and the pressure information for calculating the blood pressure value, the controller 180 may stop the calculation of the blood pressure value when the contact between the finger and the sensing module 310 is released. In this instance, the output of the alarm information may be continued or temporarily stopped based on a user setting.

The display unit 151 may output a measure screen 820 indicating the ongoing measurement of the biometric information for calculating the blood pressure value while collecting the pulse wave information and the pressure information for calculating the blood pressure value. The display unit 151 may sequentially output visual information related to the collected biometric information. Accordingly, the user can continuously contact the sensing module 310 with the finger until the biometric information is fully collected.

The controller 180 may control the display unit 151 to output blood pressure information 821 when the contact between the finger and the sensing module 310 is released or the calculation of the blood pressure value is completed. Although not illustrated in detail, the controller 180 may control the memory 170 to store the calculated blood pressure value and related information (e.g., a measured time, an additionally executed function, etc.).

Meanwhile, the controller 180 may not output the blood pressure value. The controller 180 may control the display unit 151 to output the blood pressure value by including warning information only when the blood pressure value exceeds a specific reference range.

In accordance with this exemplary embodiment, the user can be provided with a blood pressure value using biometric information which is collected while applying a control command for executing a specific function. Accordingly, the user can collect the biometric information while applying the control command for executing the specific function, even without any intentional measuring step for blood pressure measurement. This may result in obtaining blood pressure values regularly measured under a preset specific environment.

Referring to FIG. 5C, the controller 180 may switch the display unit 151 into an active state by detecting a fingerprint of a finger brought into contact with the sensing module 310. In an inactive state of the display unit 151, when a contact of a finger with the sensing module 310 is detected, the controller 180 may recognize a fingerprint of the finger by use of the light-emitting unit 313 and the light-receiving unit 314. When a prestored fingerprint image and a fingerprint image acquired by the sensing module 310 substantially match each other, the controller 180 may switch the display unit 151 into the active state. Meanwhile, when the mobile terminal 100 is in a lock mode, the controller 180 may release the lock mode based on the acquired fingerprint image.

When the lock mode is released, the display unit 151 may be switched from the inactive state into the active state, and output an authentication screen 830. However, the control step of activating the display unit or releasing the lock mode using the fingerprint information may not be limited to the illustrated example. When the lock mode is released or the display unit is switched into the active state, a specific image or a home screen page may be output.

The controller 180 may collect the pulse wave information using the light-emitting unit 313 and the light-receiving unit 314 and the pressure information using the pressure sensor 315. The fingerprint information and the pulse wave information may be simultaneously collected, but the present invention may not be limited to this.

The controller 180 may calculate the blood pressure value after completion of the authentication using the fingerprint information. When the authentication is completed, the display unit 151 may output the blood pressure information 821 including the calculated blood pressure value, but the present invention may not be limited to this.

In accordance with this exemplary embodiment, the user can be provided with a blood pressure value using biometric information, which is collected while a touch applied to a specific area (sensing module) for executing a finger scan function is maintained.

Figure 6:
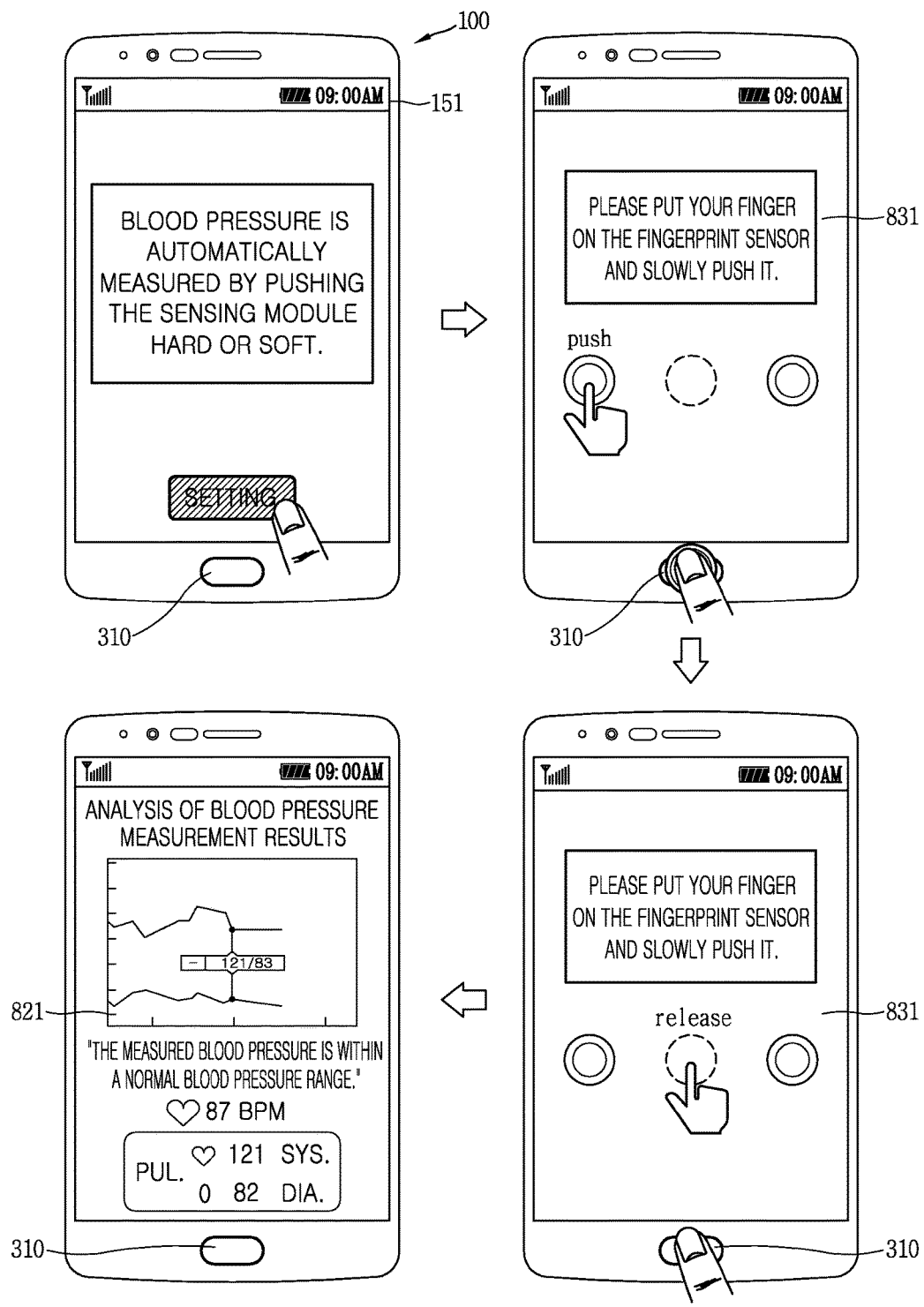
FIG. 6 is a conceptual view illustrating a method for controlling a mobile terminal in accordance with another exemplary embodiment.

FIG. 6 is a conceptual view illustrating a method for controlling a mobile terminal in accordance with another exemplary embodiment.

As illustrated in FIG. 6, the user may set whether or not to collect biometric information using a finger scan sensor (the sensing module 310) for collecting the fingerprint information. When setting the collection of the biometric information for measuring the blood pressure value through the sensing module 310, the controller 180 may control the display unit 151 to output guide information 831.

The guide information 831 may include a graphic image for guiding the user to change pressure applied according to a lapse of time. The graphic image may include a plurality of icons indicating different forces. Further referring to FIG. 4, the controller 180 may collect pulse wave information corresponding to a change in specific pressure applied by the user, and control the display unit 151 to output the blood pressure information 821 upon measuring the blood pressure value.

The controller 180 may output an icon for guiding the next pressure to be applied when pressure belonging to a reference range is sensed by the pressure sensor 315. The graphic image may output required icons according to changes in pressure. The controller 180 may control the display unit 151 not to output the graphic image any more when the required biometric information is collected.

The controller 180 may output the blood pressure information 821 including the blood pressure value, but the present invention may not be limited to this.

Figure 7A:
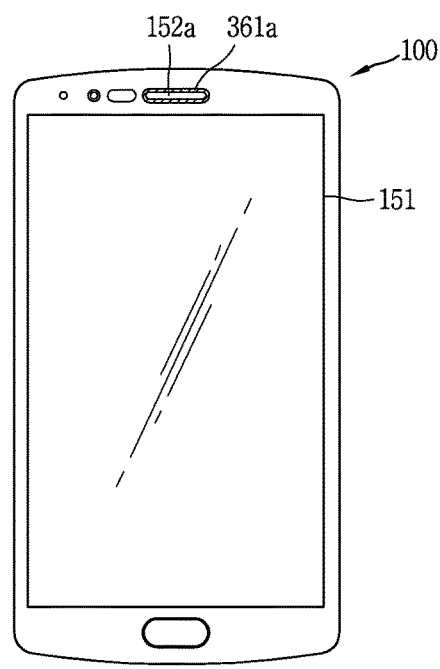
FIGS. 7A and 7B are conceptual views illustrating an ECG module in accordance with one exemplary embodiment.
Figure 7B:
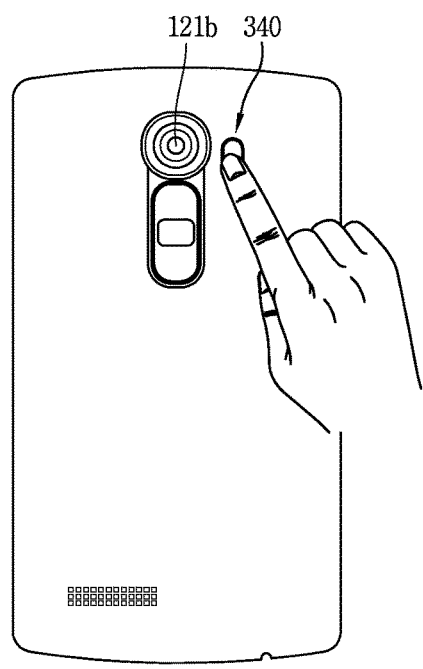
Figure 7C:
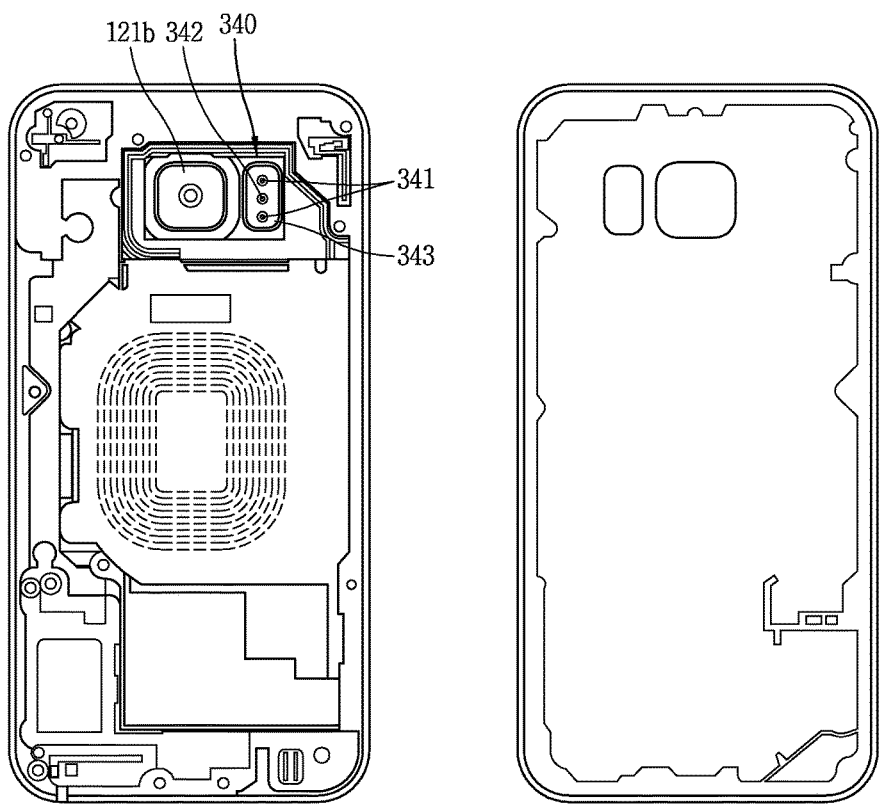
FIGS. 7C and 7D are conceptual views illustrating a sensing module.
Figure 7D:
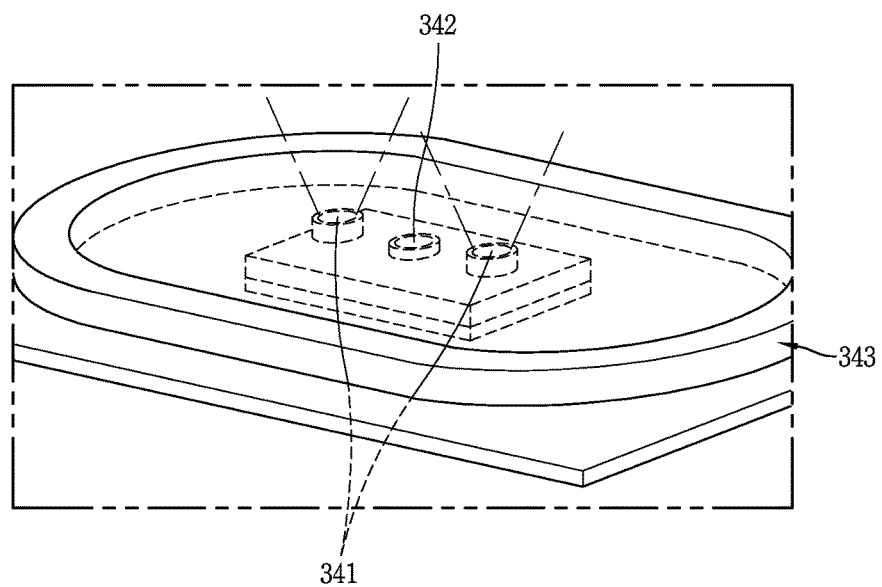

FIGS. 7A and 7B are conceptual views illustrating an electrocardiogram (ECG) module in accordance with one exemplary embodiment, and FIGS. 7C and 7D are conceptual views illustrating a sensing module. The mobile terminal according to this exemplary embodiment may measure blood pressure using pulse waves and electrocardiogram, which are acquired through a sensing module 340 and a first electrode unit 361a. One area of the sensing module 340 disclosed herein may be exposed to a rear surface of the mobile terminal 100. Here, the electrocardiogram may be records made on a skin of a body with respect to changes of potentials which are generated when heart excitement is generated and gone. That is, the electrocardiogram may correspond to information for diagnosing a motion of the heart.

The sensing module 340 may preferably be disposed adjacent to the rear camera 121b. The sensing module 340 may include a light-emitting unit 341, a light-receiving unit 342 and a second electrode unit 343. The flash may be disposed adjacent to the sensing module 340.

While the camera 121b is activated, the light-emitting unit 341 and the light-receiving unit 342 of the sensing module 340 may execute a function of measuring a distance between the mobile terminal 100 and a specific object. The controller 180 may execute auto focusing to adjust a focal point on the subject obtained by the rear camera 121b by using the distance measurement function of the light-emitting unit 341 and the light-receiving unit 342 of the sensing module 340.

For example, the light-emitting unit 341 may output laser beams. A relative distance between the mobile terminal 100 and an arbitrary subject may be measured by using a time difference that the output laser beams are reflected by the subject and come back into the light-receiving unit 342. However, a type of light emitted from the light-emitting unit 341 may not be limited to the laser beam.

Meanwhile, the controller 180 may measure pulse waves by the light-emitting unit 341 and the light-receiving unit 342. In case where a part (e.g., a finger) of the user's body is located adjacent to the sensing module 340, when light which is emitted from the light-emitting unit 341 and reflected by the body reaches the light-receiving unit 342, the controller 180 may measure pulse waves using a pattern of the incoming light of the light-receiving unit 342.

An ECG module may be configured with a pair of electrode units which come in contact with different portions of the user's body. Or, the mobile terminal 100 may include one electrode unit and an external device which is wirelessly connected to the mobile terminal 100 may include another electrode unit.

A first electrode unit 361a configuring the ECG module disclosed herein may be arranged adjacent to the audio output module 152a and a second electrode unit 343 may be disposed adjacent to the sensing module 340. The sensing module 340 according to this exemplary embodiment may include the light-emitting unit 341 that emits laser beams, and the light-receiving unit 342 that receives laser beams reflected by an arbitrary subject. The controller 180 may execute a function of adjusting a focal point of the camera 121b using incoming light.

The second electrode unit 343 may be implemented as a metal member which surrounds the light-emitting unit 341 and the light-receiving unit 342, and exposed to outside of the mobile terminal 100. The controller 180 may collect information related to pulse waves through light reflected by the user's body which is adjacent to the sensing module 340, by use of the light-emitting unit 341 and the light-receiving unit 342. That is, the sensing module 340 may function as a PPG sensor.

The sensing module according to the present invention may implement a PPG sensor for collecting pulse wave information using a configuration of measuring a distance up to a subject, and implement a part of an ECG module for measuring electrocardiogram by an additional metal member. Therefore, the pulse wave information and the electrocardiogram information can be used to measure blood pressure.

Figure 7E:
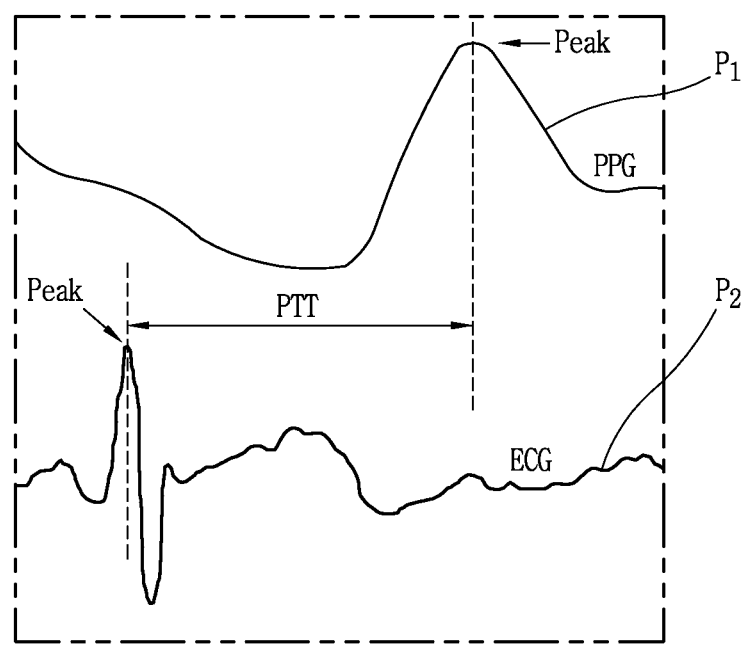
FIG. 7E is a view illustrating a method of measuring blood pressure using electrocardiogram and pulse wave information.

FIG. 7E is a view illustrating a method of measuring blood pressure using electrocardiogram and pulse wave information. The mobile terminal according to this exemplary embodiment may measure blood pressure in a cuff-less manner using electrocardiogram information and pulse wave information.

The controller 180 may measure electrocardiogram using a potential difference generated, when different portions of the user's body are brought into contact with the first and second electrode units 361a and 343. The controller 180 may calculate a blood pressure value using a pulse wave pattern P1 collected by the PPG sensor implemented as the sensing module 340, and an electrocardiogram pattern P2 collected by the ECG module configured with the first and second electrode units 361a and 343. A pulse transit time (PPT) may be measured using a time difference between a peak of the pulse wave pattern P1 and a peak of the electrocardiogram pattern P2. The controller 180 may measure blood pressure through correlation between the PPT and diastolic blood pressure.

The controller 180 may output blood pressure information 820 related to the measured blood pressure on the display unit 151 of the mobile terminal 100.

The positions of the first and second electrode units 361a and 343 disclosed herein may not be limited to those illustrated in the drawings, and may alternatively be disposed at different areas of the mobile terminal which are contactable with different portions of the user's body.

Figure 8A:
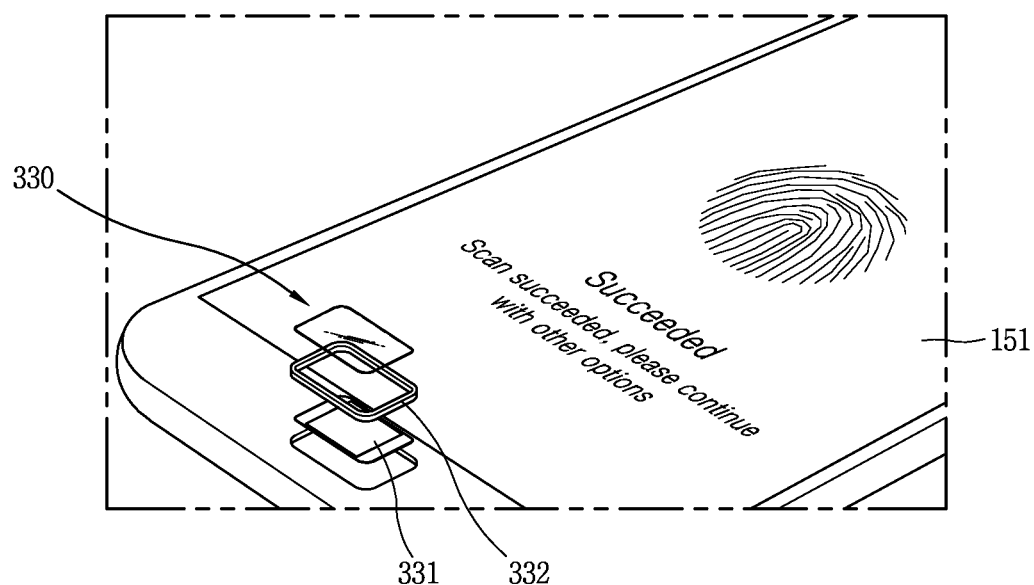
FIGS. 8A and 8B are conceptual views illustrating a sensing module capable of sensing a fingerprint in accordance with one exemplary embodiment.
Figure 8B:
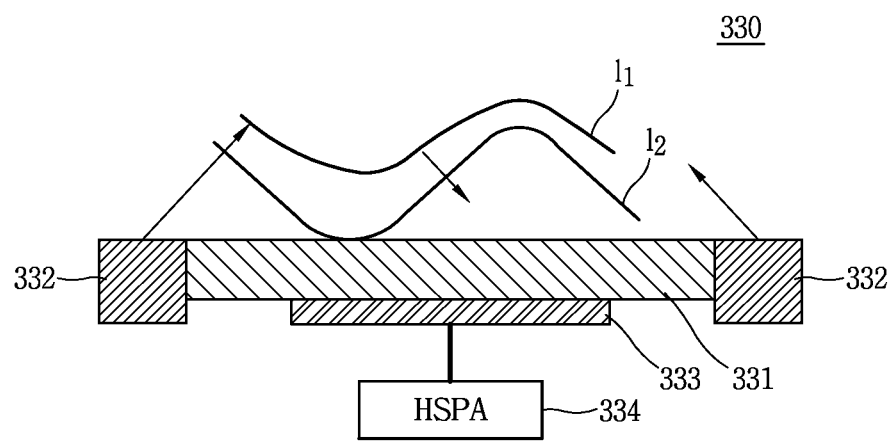

FIGS. 8A and 8B are conceptual views illustrating a sensing module capable of sensing a fingerprint in accordance with one exemplary embodiment.

As illustrated in FIGS. 8A and 8B, a sensing module 330 according to this exemplary embodiment may include first and second areas 331 and 332. The first area 331 may be configured as an Rx electrode, and the second area 332 may be configured as a Tx electrode. The first area 331 may have a preset range to facilitate a contact of the user's hand, and the second area 332 may be configured to surround an edge of the first area 331. The first and second areas 331 and 332 may be exposed to outside of the mobile terminal 100, and shapes thereof may not be limited to those illustrated in the drawings.

The sensing module 330 may recognize a fingerprint in an active capacitive manner using the first and second areas 331 and 332. An electric signal may be transmitted from the second area 332 made of a metal, and the transmitted electric signal may be reflected by curves of the fingerprint. The transmitted electric signal may pass through a dead skin I2 of a finger, reflected by a live skin I1 and be incident into the second area 332. The first area 331 which includes a pixel array 333 located beneath the second area 332 may sense a difference of capacitance of an electric signal, thereby generating a fingerprint image. The sensing module 330 may further include a high sensitive pixel amplifier (HSPA) 334.

The second area 332 may be configured as a first electrode of a pair of electrodes coming in contact with a user's body, in order to measure electrocardiogram using the potential difference. The controller 180 may measure electrocardiogram based on a potential difference, which is generated when different portions of the user's body come in contact with the second area 332 as the first electrode and a metal member mounted on another portion of the mobile terminal 100 as the second electrode, respectively.

That is, the mobile terminal disclosed herein may calculate blood pressure by using electrocardiogram, which is collected by the first electrode implemented as the second area 332 made of the metal, included in the sensing module 330 having the finger scan function, and the second electrode disposed at another area of the mobile terminal, and pulse waves collected by the PPG sensor.

As aforementioned, the sensing module may include an ECG sensor provided with electrodes brought into contact with different portions of the user's body for measuring blood pressure, and a PPG sensor including a light-emitting unit and a light-receiving unit for collecting pulse waves. Hereinafter, a sensing module disposed at one area of the mobile terminal will be described.

Figure 9A:
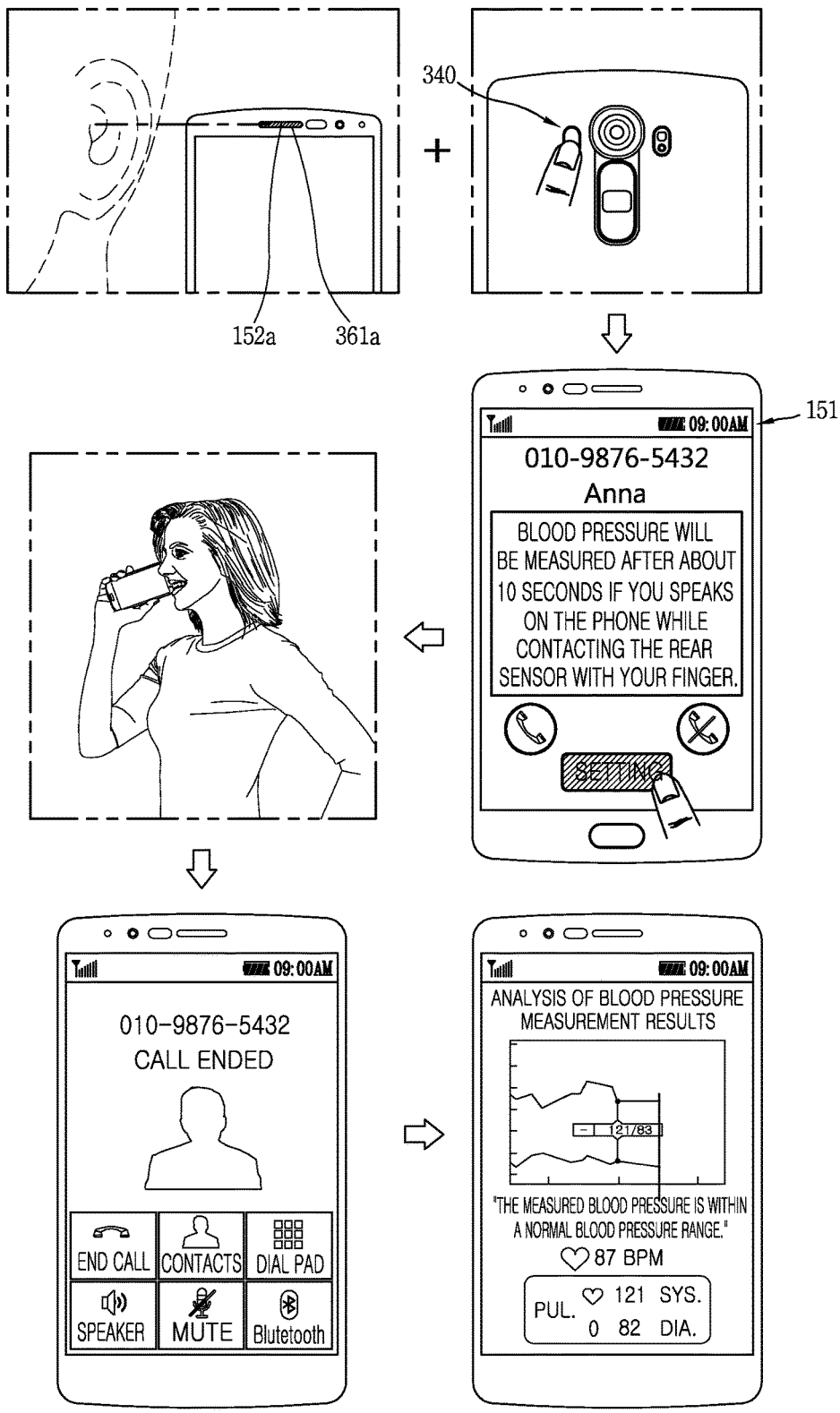
FIGS. 9A to 9C are conceptual views illustrating a method for controlling a mobile terminal in accordance with various exemplary embodiments.
Figure 9B:
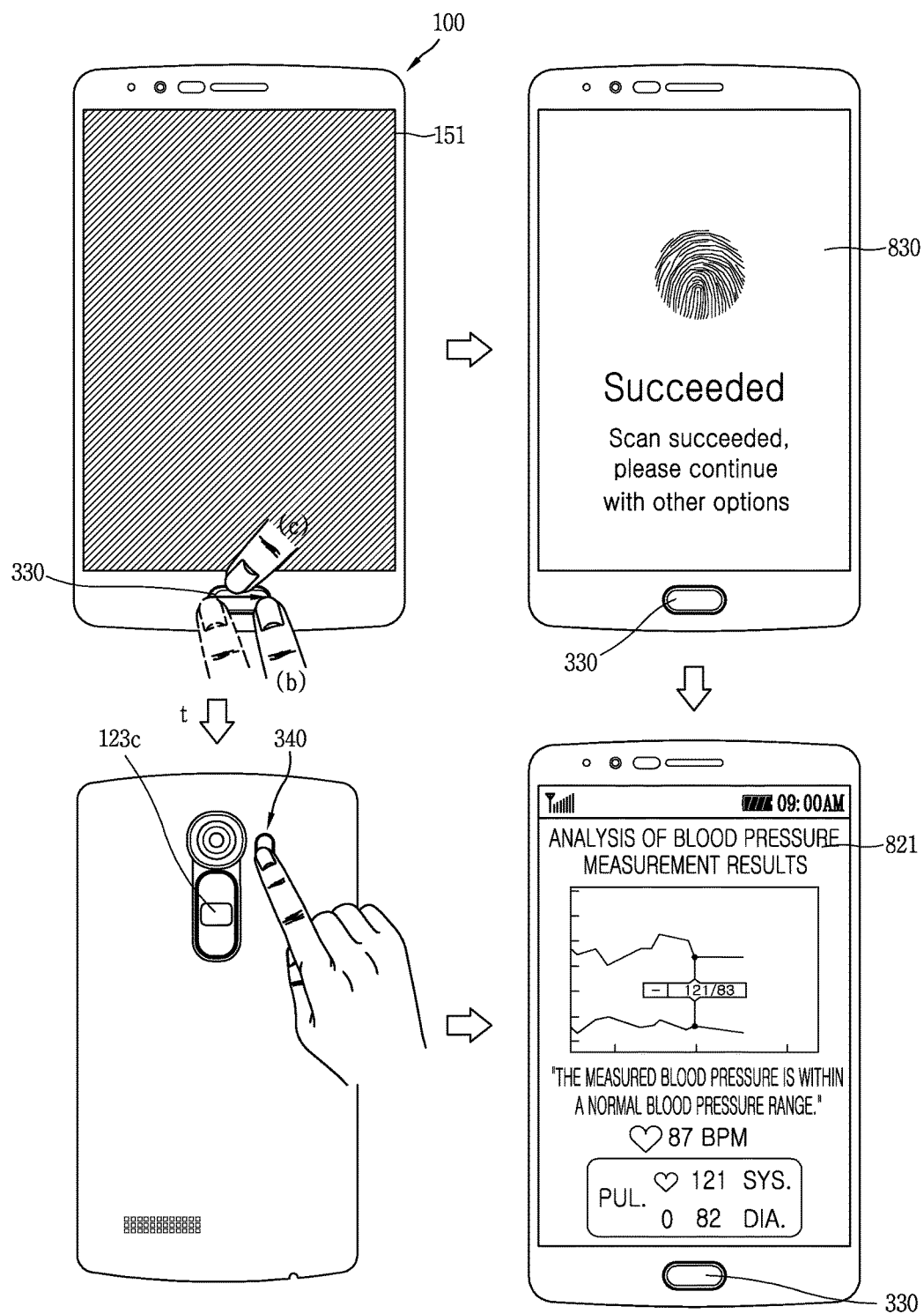
Figure 9C:
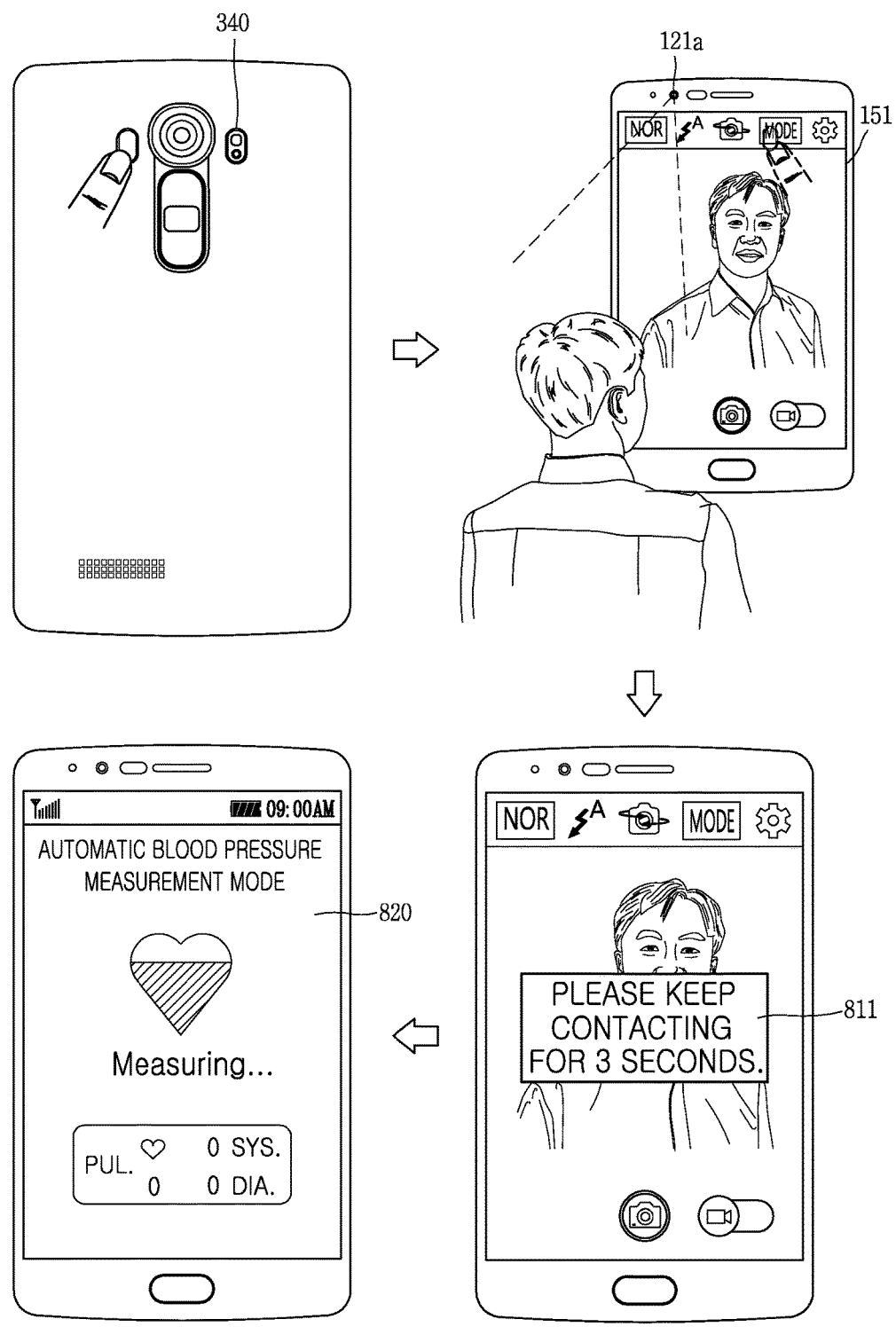

FIGS. 9A to 9C are conceptual views illustrating a control method of a mobile terminal in various exemplary embodiments.

As illustrated in FIGS. 7A, 7C and 9A, the mobile terminal according to this exemplary embodiment may include the first electrode unit 361a configured as a metal member and disposed adjacent to the audio output module 152a, and the sensing module 340 provided with the second electrode 343. The first and second electrode units 361a and 343 may configure an ECG module for collecting electrocardiogram information. The light-emitting unit 313 and the light-receiving unit 314 included in the sensing module 340 may configure a PPG sensor for measuring pulse waves.

The controller 180 may collect the pulse wave information and the electrocardiogram information through the first electrode unit 361a and the sensing module 340 when a call is connected. When the call is connected, the first electrode unit 361a may be brought into contact with the user's ear.

The display unit 151 may output guide information indicating that biometric information can be collected for measuring blood pressure, as well as a call reception screen, when the call is received. The guide information may include information related to positions of the first electrode unit 361a and the sensing module 340 for collecting the biometric information.

The controller 180 may collect the electrocardiogram information when the user's body is brought into contact with the first and second electrode units 361a and 343, and collect the pulse wave information when the sensing module 340 is brought into contact with the user's finger. The controller 180 may measure blood pressure using the electrocardiogram information and the pulse wave information while the call is connected.

Meanwhile, the controller 180 may output warning information when biometric information is not detected by the first and second electrodes 361a and 343 and the sensing module 340 while the call is connected. For example, the warning information may correspond to a voice signal, vibration and the like.

The controller 180 may control the display unit 151 to output calculated blood pressure information after the call is ended. Or, the controller 180 may control the memory 170 to store the blood pressure information along with information related to the connected call.

The controller 180 may control the display unit 151 to output the blood pressure information only when the measured blood pressure corresponds to a preset reference range or more.

According to this exemplary embodiment, sensors for collecting biometric information are disposed at areas associated with a call function. This may allow a user to collect such biometric information in response to a part of the user's body being brought into contact with a mobile terminal while a call is connected, even without an intentional contact with the electrodes and the sensing module.

Referring to FIGS. 7A, 7B, 8A, 8B and 9B, when the sensing module 330 detects a motion of a finger (b), the controller 180 may execute an authentication procedure based on sensed fingerprint information. For example, the controller 180 may release a lock mode based on the fingerprint information.

Meanwhile, when the user's finger is detected while the finger is brought into contact with the sensing module 330 (c), the controller 180 may obtain electrocardiogram information by means of the second area 332 included in the sensing module 330 and the second electrode unit 343 included in another sensing module 340, and pulse wave information by means of the light-emitting unit and the light-receiving unit of the another sensing module 340. That is, while the finger is detected by the sensing module 330 for a preset period of time, the sensing module 330 may perform a function of the electrode unit for collecting the electrocardiogram information.

Therefore, the user can control the same sensing module to perform different functions.

Hereinafter, description will be given of a control method of collecting biometric information for measuring blood pressure while a function of the front camera 121a is carried out, with reference to FIG. 9C. Referring to FIGS. 7C and 9C, the mobile terminal according to this exemplary embodiment may include the sensing module 340 disposed at the rear surface of the mobile terminal 100.

The controller 180 may execute a capturing function when a contact of a finger is detected by the light-emitting unit and the light-receiving unit of the sensing module 340 while the front camera 121*a* is activated. The mobile terminal 100 according to this exemplary embodiment may include a first electrode unit 361*a* for collecting electrocardiogram information along with the second electrode unit 343 included in the sensing module 340. For example, the first electrode may be provided adjacent to the signal input unit disposed at the front surface of the terminal main body, or included in an external device which executes wireless communication with the mobile terminal 100 and is worn on a part of the user's body.

When a control command for executing the capturing function is applied through the sensing module 340, the controller 180 may control the sensing module 340 and the second electrode 343 to execute the capturing function and collect biometric information. The controller 180 may control the display unit 151 to output guide information 811 indicating that the user's body should be continuously brought into contact with the sensing module 340 to collect the biometric information (electrocardiogram information and pulse wave information). Also, the controller 180 may control the display unit to output a measurement screen 820 indicating that the biometric information for calculating a blood pressure value is currently measured.

The controller 180 may control the memory 170 to store the measured blood pressure information along with a captured image. For example, the controller 180 may store the measured blood pressure information in a manner that text indicating the blood pressure is output on the captured image or tag the blood pressure information to the image. Although not illustrated in detail, the controller 180 may control the display unit 151 to output blood pressure information only when the calculated blood pressure value exceeds a reference range.

In accordance with the exemplary embodiment, when the sensing module 340 receives a control command for executing a specific function, the sensing module 340 may collect biometric information while performing the specific function. Also, the collected biometric information may be stored along with results of the specific function.

Figure 10A:
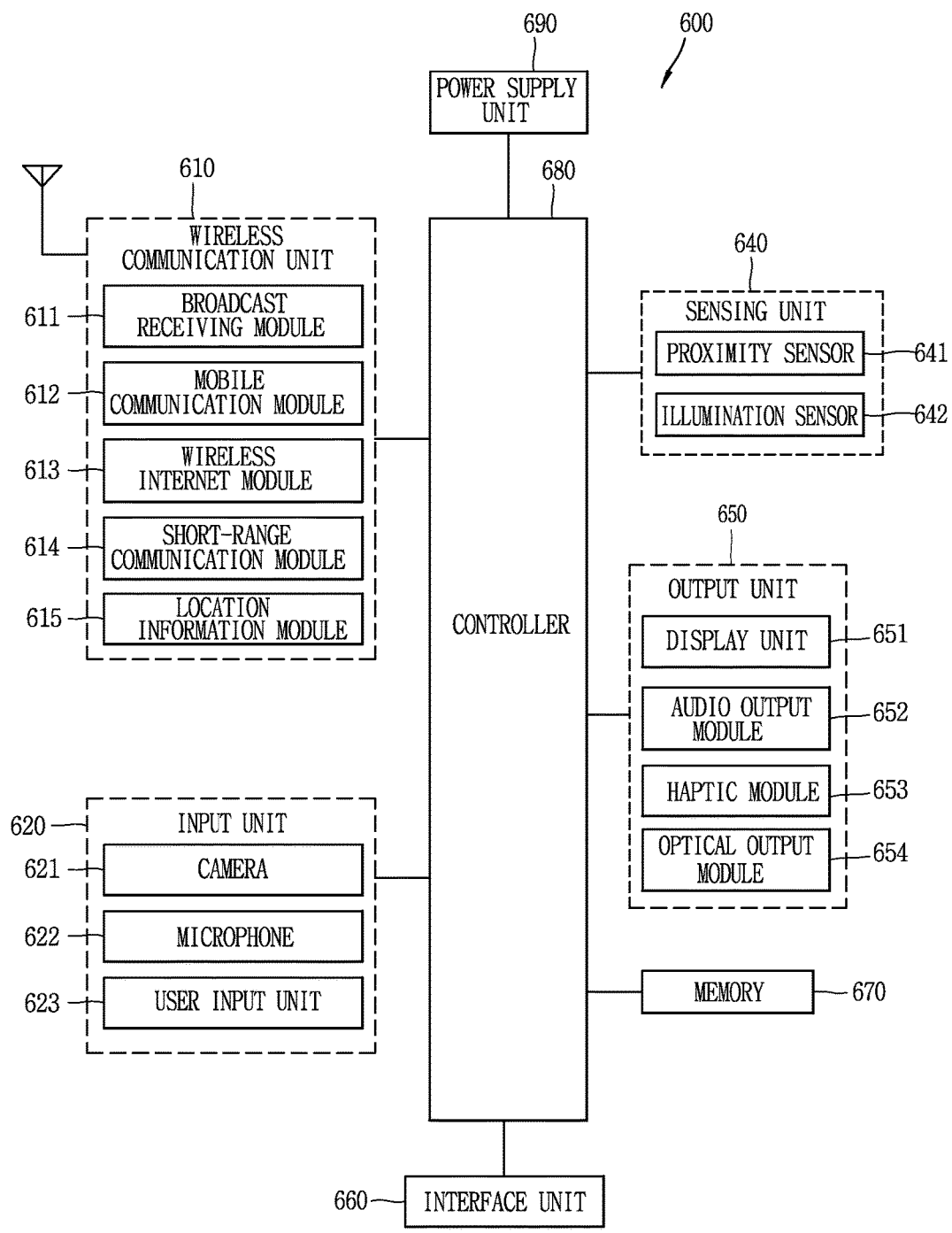
FIG. 10A is a block diagram of a mobile terminal in accordance with another exemplary embodiment.
Figure 10B:
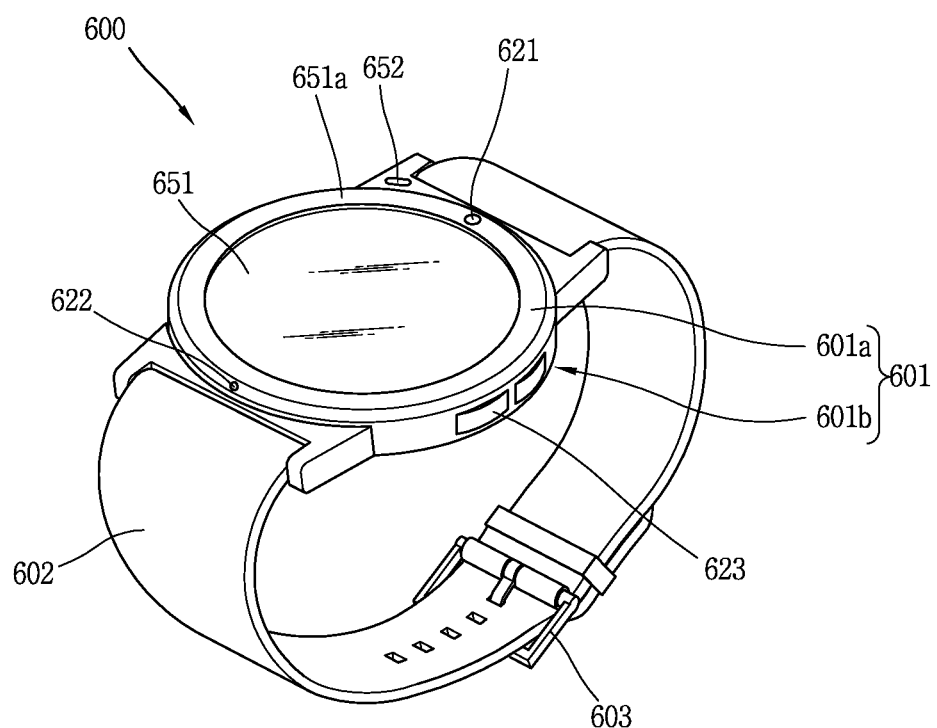
FIG. 10B is a conceptual view of one example of the mobile terminal, viewed from one direction.

FIG. 10A is a block diagram of a mobile terminal in accordance with another exemplary embodiment, and FIG. 10B is a conceptual view of one example of the mobile terminal, viewed from one direction. The mobile terminal according to this exemplary embodiment may correspond to a watch type terminal wearable on a user's wrist.

The mobile terminal 600 is shown having components such as a wireless communication unit 610, an input unit 620, a sensing unit 640, an output unit 650, an interface unit 660, a memory 670, a controller 680, and a power supply unit 690. It is understood that implementing all of the illustrated components is not a requirement, and that greater or fewer components may alternatively be implemented.

In more detail, the wireless communication unit 610 typically includes one or more modules which permit communications such as wireless communications between the mobile terminal 600 and a wireless communication system, communications between the mobile terminal 600 and another mobile terminal, communications between the mobile terminal 600 and an external server. Further, the wireless communication unit 610 typically includes one or more modules which connect the mobile terminal 600 to one or more networks.

The wireless communication unit 610 includes one or more of a broadcast receiving module 611, a mobile communication module 612, a wireless Internet module 613, a short-range communication module 614, and a location information module 615.

The input unit 620 includes a camera 621 or an image input unit for obtaining images or video, a microphone 622, which is one type of audio input device for inputting an audio signal, and a user input unit 623 (for example, a touch key, a mechanical key, and the like) for allowing a user to input information. Data (for example, audio, video, image, and the like) is obtained by the input unit 620 and may be analyzed and processed according to user commands.

The sensing unit 640 is typically implemented using one or more sensors configured to sense internal information of the mobile terminal, the surrounding environment of the mobile terminal, user information, and the like. For example, the sensing unit 640 may include at least one of a proximity sensor 641, an illumination sensor 642, a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 621), a microphone 622, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like). The mobile terminal disclosed herein may be configured to utilize information obtained from one or more sensors of the sensing unit 640, and combinations thereof.

The output unit 650 is typically configured to output various types of information, such as audio, video, tactile output, and the like. The output unit 650 is shown having at least one of a display unit 651, an audio output module 652, a haptic module 653, and an optical output module 654. The display unit 651 may have an inter-layered structure or an integrated structure with a touch sensor in order to facilitate a touch screen. The touch screen may provide an output interface between the mobile terminal 600 and a user, as well as function as the user input unit 623 which provides an input interface between the mobile terminal 600 and the user.

The interface unit 660 serves as an interface with various types of external devices that can be coupled to the mobile terminal 600. The interface unit 660, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the mobile terminal 600 may perform assorted control functions associated with a connected external device, in response to the external device being connected to the interface unit 660.

The memory 670 is typically implemented to store data to support various functions or features of the mobile terminal 600. For instance, the memory 670 may be configured to store application programs executed in the mobile terminal 600, data or instructions for operations of the mobile terminal 600, and the like. Some of these application programs may be downloaded from an external server via wireless communication. Other application programs may be installed within the mobile terminal 600 at time of manufacturing or shipping, which is typically the case for basic functions of the mobile terminal 600 (for example, receiving a call, placing a call, receiving a message, sending a message, and the like). It is common for application programs to be stored in the memory 670, installed in the mobile terminal 600, and executed by the controller 680 to perform an operation (or function) for the mobile terminal 600.

The controller 680 typically functions to control overall operation of the mobile terminal 600, in addition to the operations associated with the application programs. The controller 680 may provide or process information or functions appropriate for a user by processing signals, data, information and the like, which are input or output by the aforementioned various components, or activating application programs stored in the memory 670.

Also, the controller 680 controls some or all of the components illustrated in FIG. 10A according to the execution of an application program that have been stored in the memory 670. In addition, the controller 680 may control at least two of those components included in the mobile terminal to activate the application program.

The power supply unit 690 can be configured to receive external power or provide internal power in order to supply appropriate power required for operating elements and components included in the mobile terminal 600. The power supply unit 690 may include a battery, and the battery may be configured to be embedded in the terminal body, or configured to be detachable from the terminal body.

At least part of the components may cooperatively operate to implement an operation, a control or a control method of a mobile terminal according to various embodiments disclosed herein. Also, the operation, the control or the control method of the mobile terminal may be implemented on the mobile terminal by an activation of at least one application program stored in the memory 670.

Hereinafter, description will be given in more detail of the aforementioned components with reference to FIG. 10A, prior to describing various embodiments implemented through the mobile terminal 600.

First, regarding the wireless communication unit 610, the broadcast receiving module 611 is typically configured to receive a broadcast signal and/or broadcast associated information from an external broadcast managing entity via a broadcast channel. The broadcast channel may include a satellite channel, a terrestrial channel, or both. In some embodiments, two or more broadcast receiving modules 611 may be utilized to facilitate simultaneously receiving of two or more broadcast channels, or to support switching among broadcast channels.

The mobile communication module 612 can transmit and/or receive wireless signals to and from one or more network entities. Typical examples of a network entity include a base station, an external mobile terminal, a server, and the like. Such network entities form part of a mobile communication network, which is constructed according to technical standards or communication methods for mobile communications (for example, Global System for Mobile Communication (GSM), Code Division Multi Access (CDMA), CDMA2000 (Code Division Multi Access 2000), Enhanced Voice-Date Optimized or Enhanced Voice-Data Only (EV-DO), Wideband CDMA (WCDMA), High Speed Downlink Packet access (HSDPA), High Speed Uplink Packet Access (HSUPA), Long Term Evolution (LTE), LTE-advanced (LTE-A) and the like).

Examples of the wireless signals include audio call signals, video (telephony) call signals, or various formats of data to support communication of text and multimedia messages.

The wireless Internet module 613 is configured to facilitate wireless Internet access. This module may be internally or externally coupled to the mobile terminal 600. The wireless Internet module 63 may transmit and/or receive wireless signals via communication networks according to wireless Internet technologies.

Examples of such wireless Internet access include Wireless LAN (WLAN), Wireless Fidelity (Wi-Fi), Wi-Fi Direct, Digital Living Network Alliance (DLNA), Wireless Broadband (WiBro), Worldwide Interoperability for Microwave Access (WiMAX), High Speed Downlink Packet Access (HSDPA), High Speed Uplink Packet Access (HSUPA), Long Term Evolution (LTE), LTE-advanced (LTE-A) and the like. The wireless Internet module 113 may transmit/receive data according to one or more of such wireless Internet technologies, and other Internet technologies as well.

In some embodiments, when the wireless Internet access is implemented according to, for example, WiBro, HSDPA, HSUPA, GSM, CDMA, WCDMA, LTE, LET-A, and the like, as part of a mobile communication network, the wireless Internet module 113 may be understood as a type of the mobile communication module 612.

The short-range communication module 614 is configured to facilitate short-range communications. Suitable technologies for implementing such short-range communications include BLUETOOTH™, Radio Frequency IDentification (RFID), Infrared Data Association (IrDA), Ultra-WideBand (UWB), ZigBee, Near Field Communication (NFC), Wireless-Fidelity (Wi-Fi), Wi-Fi Direct, Wireless USB (Wireless Universal Serial Bus), and the like. The short-range communication module 114 in general supports wireless communications between the mobile terminal 600 and a wireless communication system, communications between the mobile terminal 600 and another mobile terminal 600, or communications between the mobile terminal and a network where another mobile terminal 600 (or an external server) is located, via wireless area networks. One example of the wireless area networks is a wireless personal area networks.

Here, another mobile terminal (which may be configured similarly to mobile terminal 600) may be a wearable device, for example, a smart watch, a smart glass or a head mounted display (HMD), which is able to exchange data with the mobile terminal 600 (or otherwise cooperate with the mobile terminal 600). The short-range communication module 614 may sense or recognize the wearable device, and permit communication between the wearable device and the mobile terminal 600. In addition, when the sensed wearable device is a device which is authenticated to communicate with the mobile terminal 600, the controller 680, for example, may cause transmission of at least part of data processed in the mobile terminal 600 to the wearable device via the short-range communication module 614. Hence, a user of the wearable device may use the data processed in the mobile terminal 600 on the wearable device. For example, when a call is received in the mobile terminal 600, the user may answer the call using the wearable device. Also, when a message is received in the mobile terminal 600, the user can check the received message using the wearable device.

The location information module 615 is generally configured to detect, calculate, derive or otherwise identify a position (or current position) of the mobile terminal. As an example, the location information module 615 includes a Global Position System (GPS) module, a Wi-Fi module, or both. For example, when the mobile terminal uses a GPS module, a position of the mobile terminal may be acquired using a signal sent from a GPS satellite. As another example, when the mobile terminal uses the Wi-Fi module, a position of the mobile terminal can be acquired based on information related to a wireless access point (AP) which transmits or receives a wireless signal to or from the Wi-Fi module. If desired, the location information module 615 may alternatively or additionally function with any of the other modules of the wireless communication unit 610 to obtain data related to the position of the mobile terminal. The location information module 615 is a module used for acquiring the position (or the current position) and may not be limited to a module for directly calculating or acquiring the position of the mobile terminal.

The input unit 620 may be configured to permit various types of inputs (information or signals) to the mobile terminal 600. Examples of such inputs include audio, image, video, data, and user input. Image and video input is often obtained using one or more cameras 621. Such cameras 621 may process image frames of still pictures or video obtained by image sensors in a video or image capture mode. The processed image frames can be displayed on the display unit 651 or stored in memory 670. Meanwhile, the cameras 621 may be arranged in a matrix configuration to permit a plurality of images having various angles or focal points to be input to the mobile terminal 600. Also, the cameras 621 may be located in a stereoscopic arrangement to acquire left and right images for implementing a stereoscopic image.

The microphone 622 processes an external audio signal into electric audio (sound) data. The processed audio data can be processed in various manners according to a function (or an application program) being executed in the mobile terminal 600. If desired, the microphone 622 may include assorted noise removing algorithms to remove unwanted noise generated in the course of receiving the external audio signal.

The user input unit 623 is a component that permits input by a user. Such user input may enable the controller 680 to control operation of the mobile terminal 600. The user input unit 623 may include one or more of a mechanical input element (for example, a mechanical key, a button located on a front and/or rear surface or a side surface of the mobile terminal 600, a dome switch, a jog wheel, a jog switch, and the like), or a touch-sensitive input element, among others. As one example, the touch-sensitive input element may be a virtual key, a soft key or a visual key, which is displayed on a touch screen through software processing, or a touch key which is located on the mobile terminal at a location that is other than the touch screen. On the other hand, the virtual key or the visual key may be displayed on the touch screen in various shapes, for example, graphic, text, icon, video, or a combination thereof.

The sensing unit 640 is generally configured to sense one or more of internal information of the mobile terminal, surrounding environment information of the mobile terminal, user information, or the like, and generate a corresponding sensing signal. The controller 680 generally cooperates with the sending unit 640 to control operation of the mobile terminal 600 or execute data processing, a function or an operation associated with an application program installed in the mobile terminal based on the sensing signal. The sensing unit 640 may be implemented using any of a variety of sensors, some of which will now be described in more detail.

The proximity sensor 641 refers to a sensor to sense presence or absence of an object approaching a surface, or an object located near a surface, by using an electromagnetic field, infrared rays, or the like without a mechanical contact. The proximity sensor 641 may be arranged at an inner region of the mobile terminal covered by the touch screen, or near the touch screen.

The proximity sensor 641, for example, may include any of a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and the like. When the touch screen is implemented as a capacitance type, the proximity sensor 641 can sense proximity of a pointer relative to the touch screen by changes of an electromagnetic field, which is responsive to an approach of an object with conductivity. In this case, the touch screen (touch sensor) may also be categorized as a proximity sensor.

The term "proximity touch" will often be referred to herein to denote the scenario in which a pointer is positioned to be proximate to the touch screen without contacting the touch screen. The term "contact touch" will often be referred to herein to denote the scenario in which a pointer makes physical contact with the touch screen. For the position corresponding to the proximity touch of the pointer relative to the touch screen, such position will correspond to a position where the pointer is perpendicular to the touch screen. The proximity sensor 641 may sense proximity touch, and proximity touch patterns (for example, distance, direction, speed, time, position, moving status, and the like). In general, controller 680 processes data corresponding to proximity touches and proximity touch patterns sensed by the proximity sensor 641, and cause output of visual information on the touch screen. In addition, the controller 680 can control the mobile terminal 600 to execute different operations or process different data (or information) according to whether a touch with respect to a point on the touch screen is either a proximity touch or a contact touch.

A touch sensor can sense a touch (or a touch input) applied to the touch screen, such as display unit 651, using any of a variety of touch methods. Examples of such touch methods include a resistive type, a capacitive type, an infrared type, and a magnetic field type, among others.

As one example, the touch sensor may be configured to convert changes of pressure applied to a specific part of the display unit 651, or convert capacitance occurring at a specific part of the display unit 651, into electric input signals. The touch sensor may also be configured to sense not only a touched position and a touched region, but also touch pressure and/or touch capacitance. A touch object is generally used to apply a touch input to the touch sensor. Examples of typical touch objects include a finger, a touch pen, a stylus pen, a pointer, or the like.

When a touch input is sensed by a touch sensor, corresponding signals may be transmitted to a touch controller. The touch controller may process the received signals, and then transmit corresponding data to the controller 680. Accordingly, the controller 680 may sense which region of the display unit 651 has been touched. Here, the touch controller may be a component separate from the controller 680, the controller 680, and combinations thereof.

Meanwhile, the controller 680 may execute the same or different controls according to a type of touch object that touches the touch screen or a touch key provided in addition to the touch screen. Whether to execute the same or different control according to the object which provides a touch input may be decided based on a current operating state of the mobile terminal 600 or a currently executed application program, for example.

The touch sensor and the proximity sensor may be implemented individually, or in combination, to sense various types of touches. Such touches includes a short (or tap) touch, a long touch, a multi-touch, a drag touch, a flick touch, a pinch-in touch, a pinch-out touch, a swipe touch, a hovering touch, and the like.

If desired, an ultrasonic sensor may be implemented to recognize position information relating to a touch object using ultrasonic waves. The controller 680, for example, may calculate a position of a wave generation source based on information sensed by an illumination sensor and a plurality of ultrasonic sensors. Since light is much faster than ultrasonic waves, the time for which the light reaches the optical sensor is much shorter than the time for which the ultrasonic wave reaches the ultrasonic sensor. The position of the wave generation source may be calculated using this fact. For instance, the position of the wave generation source may be calculated using the time difference from the time that the ultrasonic wave reaches the sensor based on the light as a reference signal.

The camera 621, which has been depicted as a component of the input unit 620, typically includes at least one a camera sensor (CCD, CMOS etc.), a photo sensor (or image sensors), and a laser sensor.

Implementing the camera 621 with a laser sensor may allow detection of a touch of a physical object with respect to a 3D stereoscopic image. The photo sensor may be laminated on, or overlapped with, the display device. The photo sensor may be configured to scan movement of the physical object in proximity to the touch screen. In more detail, the photo sensor may include photo diodes and transistors at rows and columns to scan content received at the photo sensor using an electrical signal which changes according to the quantity of applied light. Namely, the photo sensor may calculate the coordinates of the physical object according to variation of light to thus obtain position information of the physical object.

The display unit 651 is generally configured to output information processed in the mobile terminal 600. For example, the display unit 651 may display execution screen information of an application program executing at the mobile terminal 600 or user interface (UI) and graphic user interface (GUI) information in response to the execution screen information.

Also, the display unit 651 may be implemented as a stereoscopic display unit for displaying stereoscopic images.

A typical stereoscopic display unit may employ a stereoscopic display scheme such as a stereoscopic scheme (a glass scheme), an auto-stereoscopic scheme (glassless scheme), a projection scheme (holographic scheme), or the like.

The audio output module 652 is generally configured to output audio data. Such audio data may be obtained from any of a number of different sources, such that the audio data may be received from the wireless communication unit 610 or may have been stored in the memory 670. The audio data may be output during modes such as a signal reception mode, a call mode, a record mode, a voice recognition mode, a broadcast reception mode, and the like. The audio output module 652 can provide audible output related to a particular function (e.g., a call signal reception sound, a message reception sound, etc.) performed by the mobile terminal 600. The audio output module 652 may also be implemented as a receiver, a speaker, a buzzer, or the like.

A haptic module 653 can be configured to generate various tactile effects that a user feels, perceive, or otherwise experience. A typical example of a tactile effect generated by the haptic module 653 is vibration. The strength, pattern and the like of the vibration generated by the haptic module 653 can be controlled by user selection or setting by the controller. For example, the haptic module 653 may output different vibrations in a combining manner or a sequential manner.

Besides vibration, the haptic module 653 can generate various other tactile effects, including an effect by stimulation such as a pin arrangement vertically moving to contact skin, a spray force or suction force of air through a jet orifice or a suction opening, a touch to the skin, a contact of an electrode, electrostatic force, an effect by reproducing the sense of cold and warmth using an element that can absorb or generate heat, and the like.

The haptic module 653 can also be implemented to allow the user to feel a tactile effect through a muscle sensation such as the user's fingers or arm, as well as transferring the tactile effect through direct contact. Two or more haptic modules 653 may be provided according to the particular configuration of the mobile terminal 600.

An optical output module 654 can output a signal for indicating an event generation using light of a light source. Examples of events generated in the mobile terminal 600 may include message reception, call signal reception, a missed call, an alarm, a schedule alarm, an email reception, information reception through an application, and the like.

A signal output by the optical output module 654 may be implemented in such a manner that the mobile terminal emits monochromatic light or light with a plurality of colors. The signal output may be terminated as the mobile terminal senses that a user has checked the generated event, for example.

The interface unit 660 serves as an interface for external devices to be connected with the mobile terminal 600. For example, the interface unit 660 can receive data transmitted from an external device, receive power to transfer to elements and components within the mobile terminal 600, or transmit internal data of the mobile terminal 600 to such external device. The interface unit 660 may include wired or wireless headset ports, external power supply ports, wired or wireless data ports, memory card ports, ports for connecting a device having an identification module, audio input/output (I/O) ports, video I/O ports, earphone ports, or the like.

The identification module may be a chip that stores various information for authenticating authority of using the mobile terminal 600 and may include a user identity module (UIM), a subscriber identity module (SIM), a universal subscriber identity module (USIM), and the like. In addition, the device having the identification module (also referred to herein as an "identifying device") may take the form of a smart card. Accordingly, the identifying device can be connected with the terminal 600 via the interface unit 660.

When the mobile terminal 600 is connected with an external cradle, the interface unit 660 can serve as a passage to allow power from the cradle to be supplied to the mobile terminal 600 or may serve as a passage to allow various command signals input by the user from the cradle to be transferred to the mobile terminal there through. Various command signals or power input from the cradle may operate as signals for recognizing that the mobile terminal is properly mounted on the cradle.

The memory 670 can store programs to support operations of the controller 680 and store input/output data (for example, phonebook, messages, still images, videos, etc.). The memory 670 may store data related to various patterns of vibrations and audio which are output in response to touch inputs on the touch screen.

The memory 670 may include one or more types of storage mediums including a flash memory type, a hard disk type, a solid state disk (SSD) type, a silicon disk drive (SDD) type, a multimedia card micro type, a card-type memory (e.g., SD or DX memory, etc), a Random Access Memory (RAM), a Static Random Access Memory (SRAM), a Read-Only Memory (ROM), an Electrically Erasable Programmable Read-Only Memory (EEPROM), a Programmable Read-Only memory (PROM), a magnetic memory, a magnetic disk, an optical disk, and the like. The mobile terminal 600 may also be operated in relation to a network storage device that performs the storage function of the memory 670 over a network, such as the Internet.

The controller 680 may typically control the general operations of the mobile terminal 600. For example, the controller 680 may set or release a lock state for restricting a user from inputting a control command with respect to applications when a status of the mobile terminal meets a preset condition.

The controller 680 can also perform the controlling and processing associated with voice calls, data communications, video calls, and the like, or perform pattern recognition processing to recognize a handwriting input or a picture drawing input performed on the touch screen as characters or images, respectively. In addition, the controller 680 can control one or a combination of those components in order to implement various exemplary embodiments disclosed herein.

The power supply unit 690 receives external power or provide internal power and supply the appropriate power required for operating respective elements and components included in the mobile terminal 600. The power supply unit 690 may include a battery, which is typically rechargeable or be detachably coupled to the terminal body for charging.

The power supply unit 690 may include a connection port. The connection port may be configured as one example of the interface unit 660 to which an external charger for supplying power to recharge the battery is electrically connected.

As another example, the power supply unit 690 may be configured to recharge the battery in a wireless manner without use of the connection port. In this example, the power supply unit 690 can receive power, transferred from an external wireless power transmitter, using at least one of an inductive coupling method which is based on magnetic induction or a magnetic resonance coupling method which is based on electromagnetic resonance.

Various embodiments described herein may be implemented in a computer-readable medium, a machine-readable medium, or similar medium using, for example, software, hardware, or any combination thereof.

Referring to FIG. 10B, the watch-type mobile terminal 600 includes a main body 601 with a display unit 651 and a band 602 connected to the main body 601 to be wearable on a wrist.

The main body 601 may include a case having a certain appearance. As illustrated, the case may include a first case 601a and a second case 601b cooperatively defining an inner space for accommodating various electronic components. Other configurations are possible. For instance, a single case may alternatively be implemented, with such a case being configured to define the inner space, thereby implementing a mobile terminal 600 with a uni-body.

The watch-type mobile terminal 600 can perform wireless communication, and an antenna for the wireless communication can be installed in the main body 601. The antenna may extend its function using the case. For example, a case including a conductive material may be electrically connected to the antenna to extend a ground area or a radiation area.

The display unit 651 is shown located at the front side of the main body 601 so that displayed information is viewable to a user. The display unit 651 includes a touch sensor so that the display unit can function as a touch screen. As illustrated, a window 651a is positioned on the first case 601a to form a front surface of the terminal body together with the first case 601a.

The main body 601 includes audio output module 652, a camera 621, a microphone 622, and a user input unit 623 positioned on the main body 601. When the display unit 651 is implemented as a touch screen, it may function as the user input unit 623, and a separate key may thus not be provided on the main body 601.

The band 602 is commonly worn on the user's wrist and may be made of a flexible material for facilitating wearing of the device. As one example, the band 602 may be made of fur, rubber, silicon, synthetic resin, or the like. The band 602 may also be configured to be detachable from the main body 601. Accordingly, the band 602 may be replaceable with various types of bands according to a user's preference.

Meanwhile, the band 602 may be used for extending the performance of the antenna. For example, the band may include therein a ground extending portion (not shown) electrically connected to the antenna to extend a ground area.

The band 602 may include fastener 603. The fastener 603 may be implemented into a buckle type, a snap-fit hook structure, a Velcro® type, or the like, and include a flexible section or material. The drawing illustrates an example that the fastener 603 is implemented using a buckle.

Figure 11A:
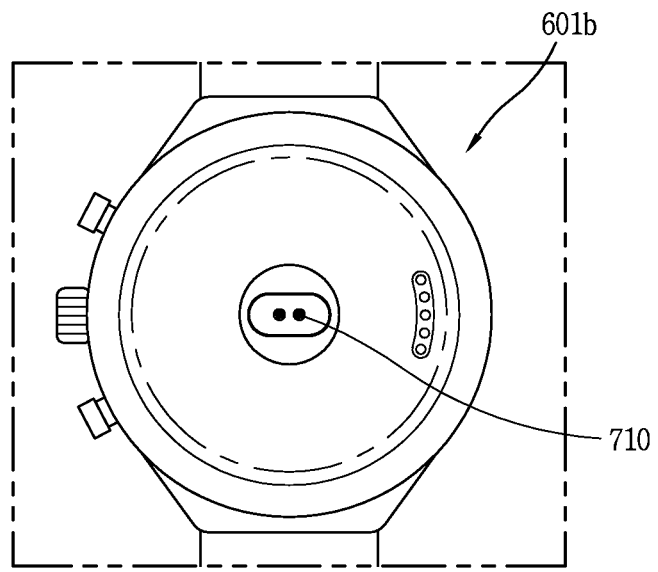
FIG. 11A is a conceptual view illustrating a sensing module for measuring blood pressure in accordance with one exemplary embodiment.
Figure 11B:
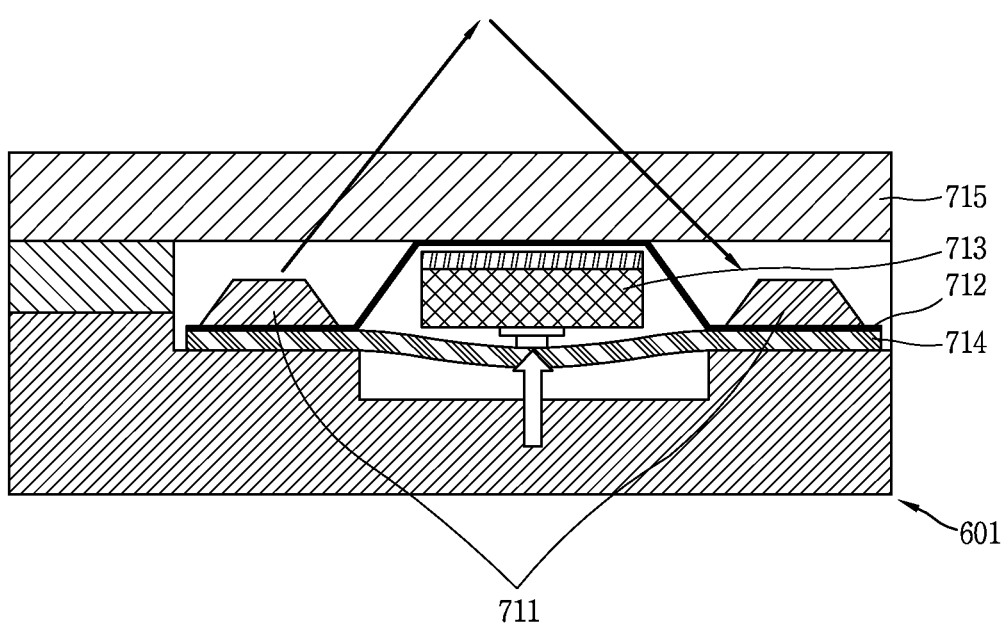
FIG. 11B is a conceptual view illustrating components of the sensing module of FIG. 11A.
Figure 11C:
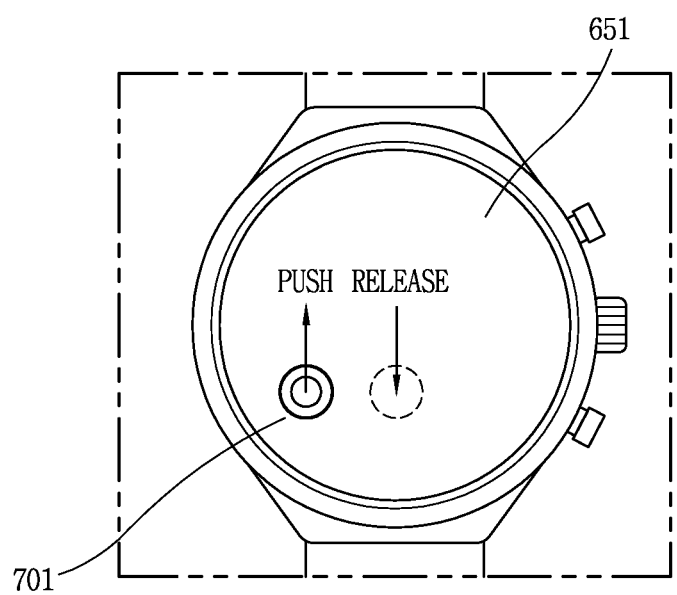
FIG. 11C is a conceptual view illustrating a control method of outputting guide information while measuring blood pressure using the sensing module of FIG. 11A.

FIG. 11A is a conceptual view illustrating a sensing module for measuring blood pressure in accordance with one exemplary embodiment, FIG. 11B is a conceptual view illustrating components of the sensing module, and FIG. 11C is a conceptual view illustrating a control method of outputting guide information while measuring blood pressure. The mobile terminal according to this exemplary embodiment may employ a method of collecting pressure and pulse wave information through a sensing module, and measuring blood pressure based on a periodic open state of arterial blood vessels when a cuff is pressed and released.

Referring to FIG. 11A, a sensing module 710 according to this exemplary embodiment may be disposed such that one area thereof is exposed by the second case 601b. The sensing module 710, as illustrated in FIG. 11B, may include a light-emitting unit 711, a light-receiving unit 712, a pressure sensor 713, an elastic supporting unit 714, and a window 715.

The light-emitting unit 711 and the light-receiving unit 712 may be covered with the window 715. The light-emitting unit 711 may be configured as a green LED emitting green light but may not be limited to this. When the user wears the mobile terminal 600, the window 715 may be located to face the user's wrist. Accordingly, when light emitted from the light-emitting unit 711 is reflected by the user's body, the light-receiving unit 712 may sense the reflected light.

The controller may determine whether or not the user is wearing the mobile terminal 600 using the light sensed by the light-receiving unit 712, and perform a specific function according to the determination result.

Meanwhile, the controller may collect pulse wave information using a pattern of light sensed by the light-receiving unit 712. That is, the light-emitting unit 711 and the light-receiving unit 712 may be configured as a PPG sensor measuring the pulse waves.

The pressure sensor 713 may sense an external force applied from outside of the mobile terminal 600. When an external force is applied to the first case 601a or the display unit 651 while the mobile terminal 600 is worn on the user's wrist, a space between the first and second cases 601a and 601b may be reduced and the pressure sensor 713 may sense the external force. When the external force is applied, the light-emitting unit 711 and the light-receiving unit 712 may be more closely adhered to the user's body, which may result in changing an amount of incoming light which is reflected by the user's skin.

The elastic supporting unit 714 may be configured as a leaf spring, but not be limited to this. The elastic supporting unit 714 may provide an elastic restoring force when the external force is released.

The display unit 651, as illustrated in FIG. 11C, may output guide information 701 for guiding the user to apply or release an external force during collection of the pulse waves. The guide information 701 may be an image and/or text for notifying the need of applying or releasing pressure at a specific time interval.

FIGS. 12A to 12D are conceptual views illustrating a mobile terminal having an electrode unit for measuring electrocardiogram according to various exemplary embodiments. The mobile terminal according to this exemplary embodiment may measure blood pressure using measured pulse wave information and electrocardiogram information. Hereinafter, an electrode unit disposed at a specific area of the mobile terminal will be described according to various exemplary embodiments. The mobile terminal according to the various exemplary embodiments may include a PPG sensor provided with a light-emitting unit and a light-receiving unit for measuring pulse waves.

Figure 12A:
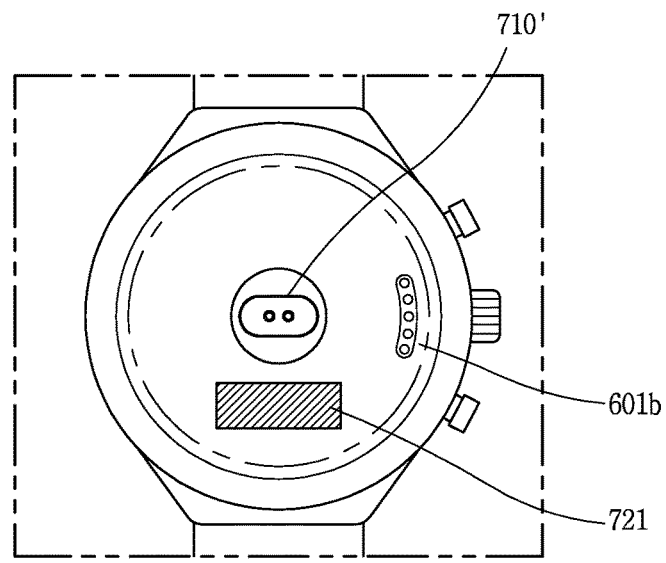
FIGS. 12A to 12D are conceptual views illustrating a mobile terminal having an electrode unit for measuring electrocardiogram.

Referring to FIG. 12A, an electrode unit 721 according to this exemplary embodiment may be provided at the second case 601b. The electrode unit 721 may be disposed adjacent to a PPG sensor 710' which includes the light-emitting unit and the light-receiving unit. The electrode unit 721 may be disposed at the second case 601b, which is externally exposed, so as to be brought into contact with the user's skin when the mobile terminal 600 is worn on the user's wrist.

Figure 12B:
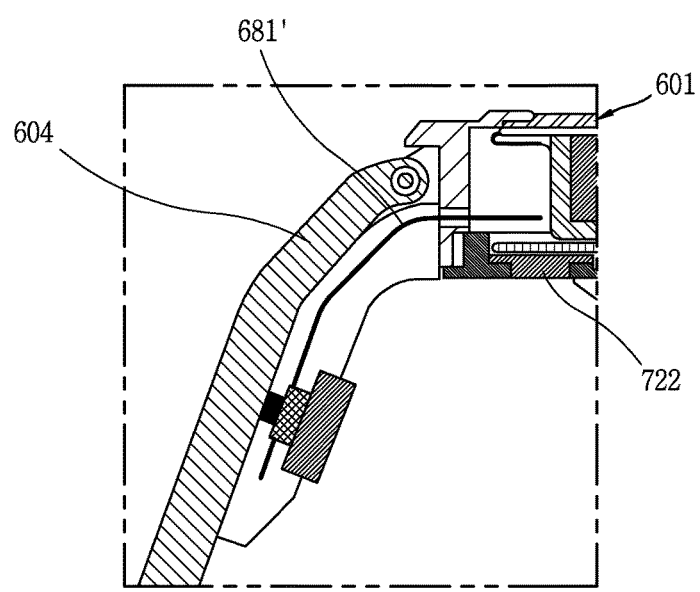

Referring to FIG. 12B, an electrode unit 722 according to this exemplary embodiment may be provided on one surface of the band 604. For example, the electrode unit 722 may be provided on one surface of the band 604, which is brought into contact with the user's skin when the mobile terminal 600 is worn, but may not be limited to this.

The electrode unit 722 may be disposed to be exposed to an outer surface of the band 604. The band 604 may include a flexible printed circuit board 681' which electrically connects the electrode unit 722 and the main body 601 to each other. The flexible printed circuit board 681' may be located in the band 604.

Figure 12C:
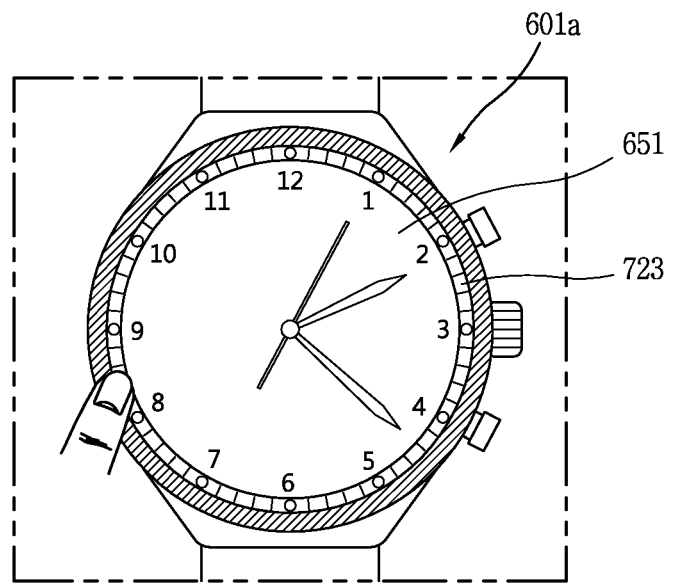

Referring to FIG. 12C, an electrode unit 723 according to this exemplary embodiment may be provided to surround at least one area of an edge of the display unit 651. That is, the electrode unit 723 may be mounted to the first case 601a. According to this exemplary embodiment, a part (e.g., a hand) of the user's body may be more easily contactable with the electrode unit 723 while the mobile terminal is worn.

Figure 12D:
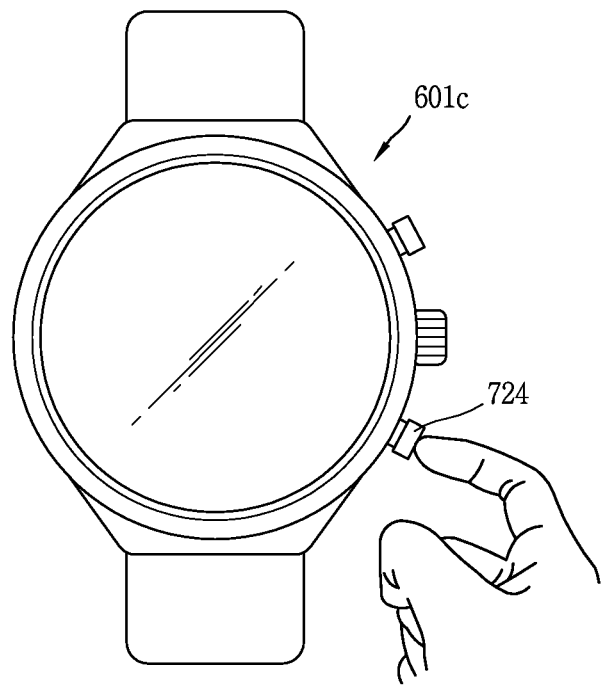

Referring to FIG. 12D, an electrode unit 724 according to this exemplary embodiment may be provided at a stem portion 601c which allows for inputting a control command corresponding to a specific function. The stem portion 601c may be drawn out of or inserted into the main body in a state of being connected to the main body. The stem portion 601c may also be rotatable in a bidirectional manner. The mobile terminal 600 may include a plurality of stem portions.

The mobile terminal according to this exemplary embodiment may measure electrocardiogram when the user's hand comes in contact with the stem portion 601c for executing a specific function.

The electrode units according to the aforementioned various exemplary embodiments may be applied to the mobile terminal in a combining manner. For example, the electrode units illustrated in FIGS. 12A and 12D may be included in one mobile terminal.

Figure 13A:
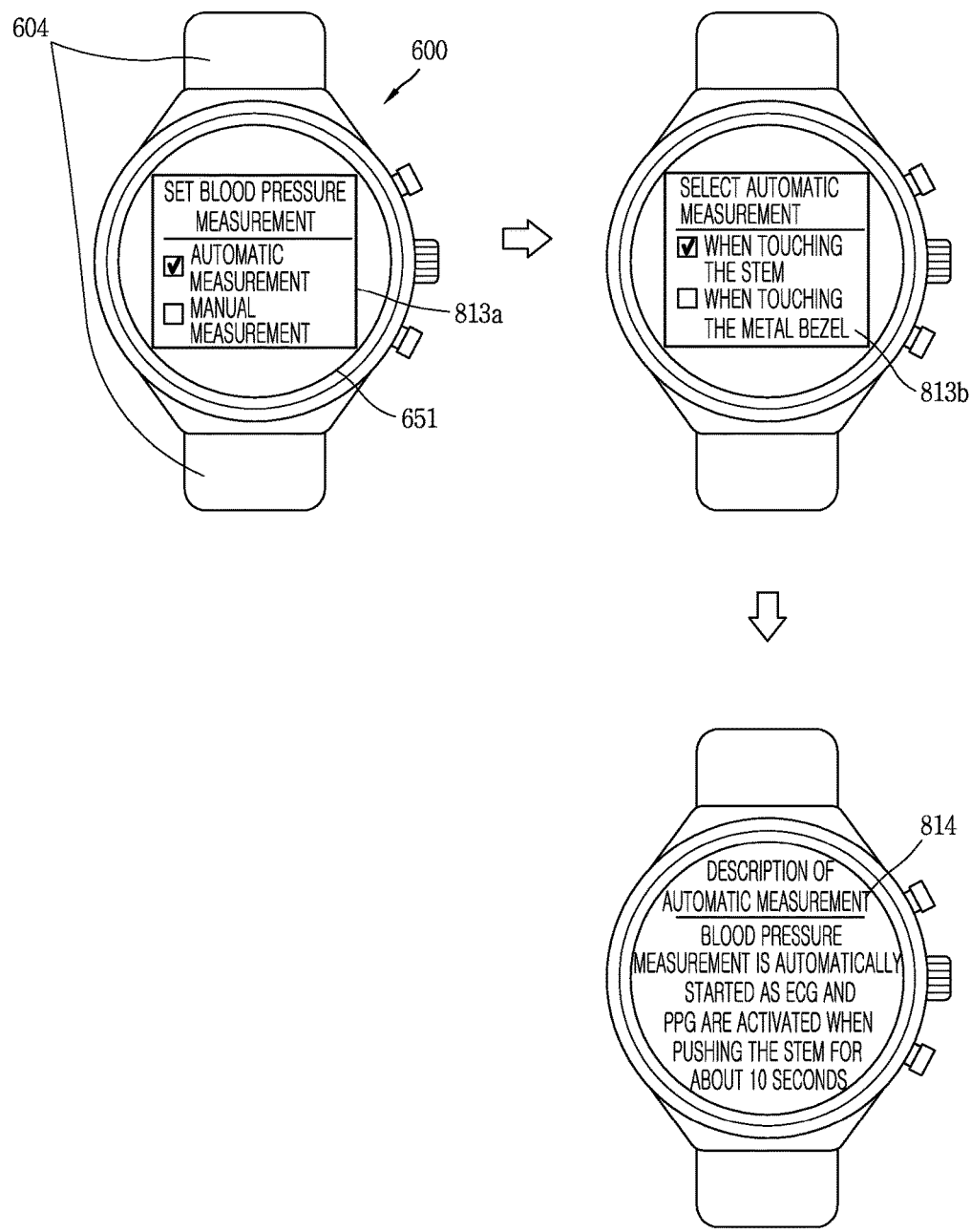
FIGS. 13A to 13C are conceptual views illustrating a method for controlling a watch-type terminal in accordance with one exemplary embodiment.
Figure 13B:
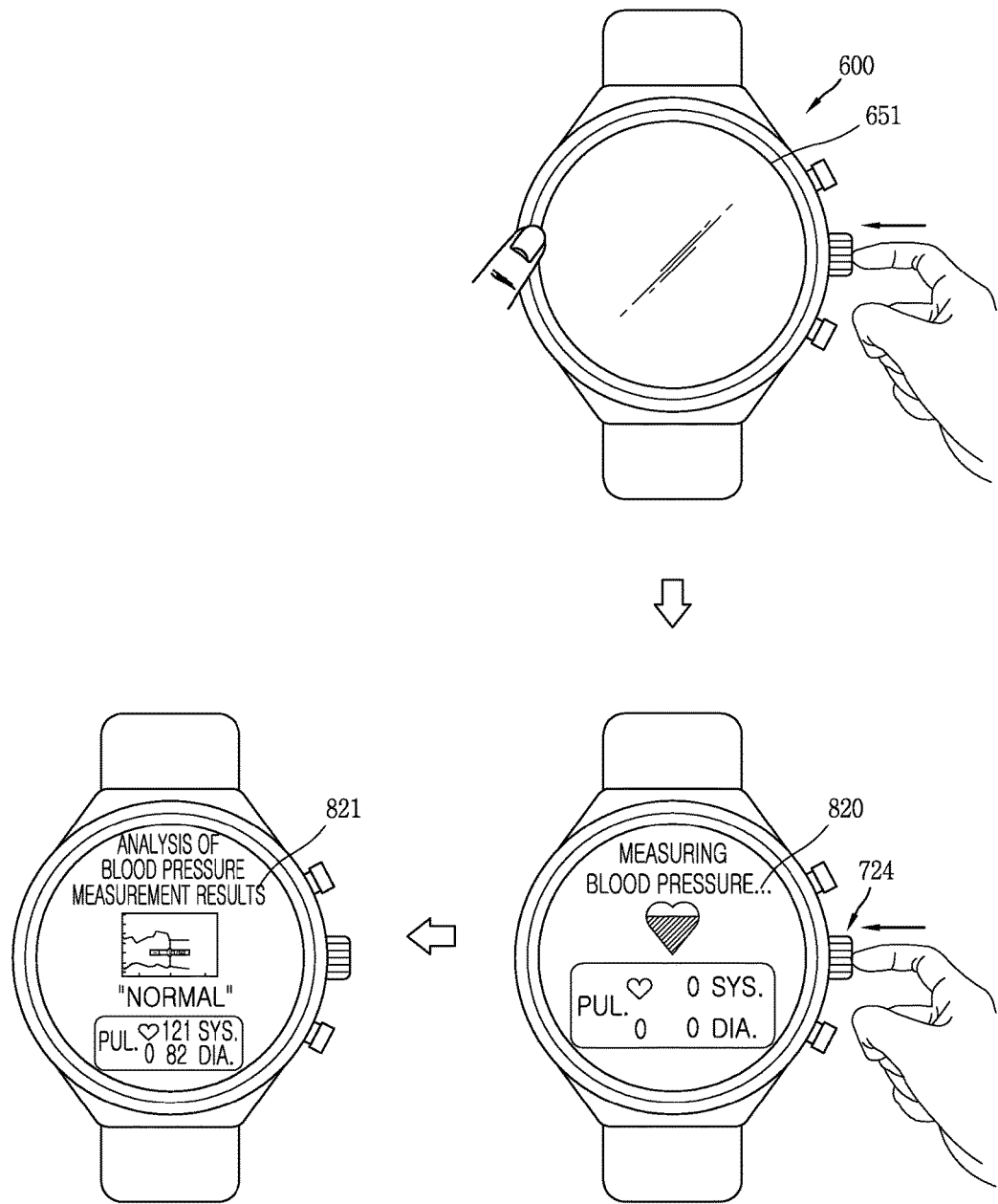
Figure 13C:
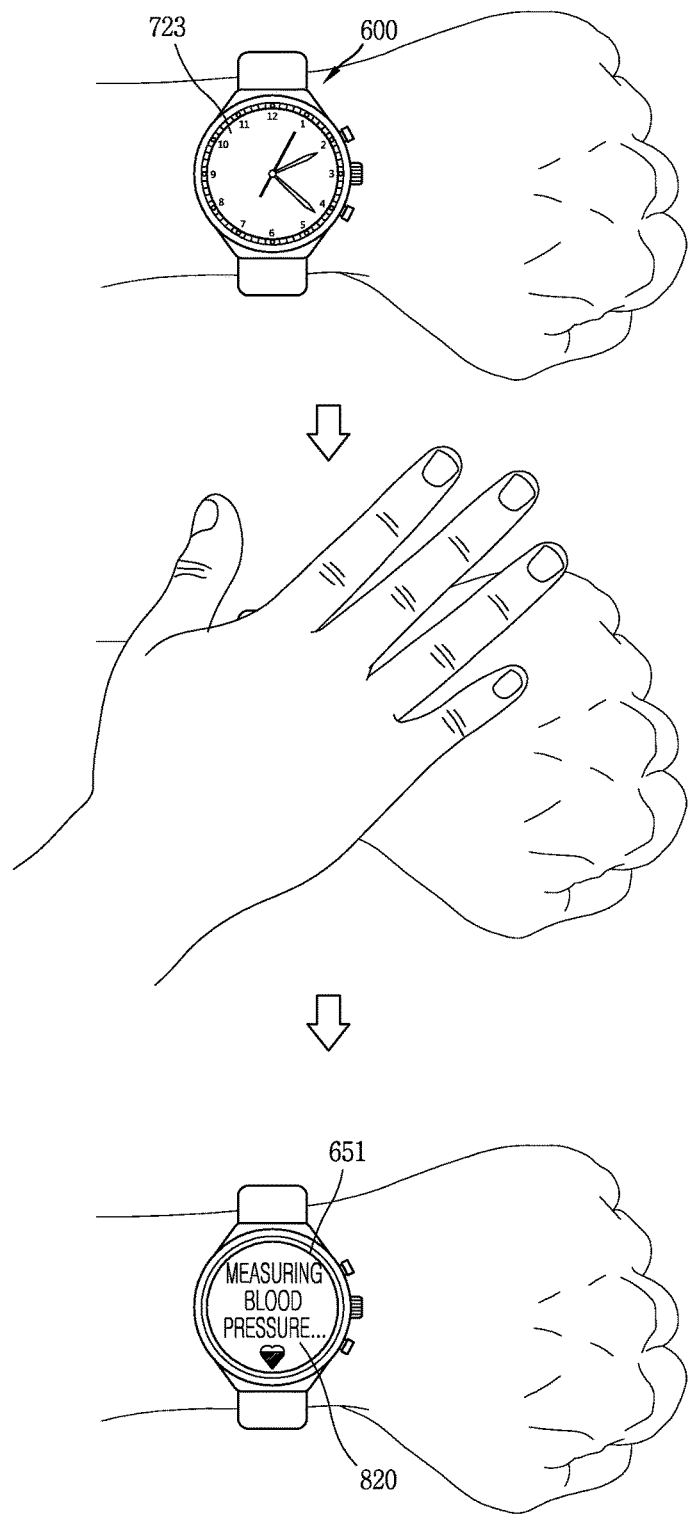

FIGS. 13A to 13C are conceptual views illustrating a method for controlling a watch-type terminal in accordance with one exemplary embodiment.

Referring to FIG. 13A, the controller may set an automatic blood pressure measurement or a manual blood pressure measurement based on a user's control command. For example, the display unit 651 may output a first select window 813a for selecting the automatic or manual measurement on a setting screen for measuring biometric information, in a state that power is initially on or a collection of the biometric information is initially controlled.

The mobile terminal may include a plurality of electrode units for measuring electrocardiogram information at different areas. When the automatic measurement is set, the display unit 651 may output a second select window 813b to select an electrode unit for measuring the electrocardiogram.

The display unit 651 may output guide information 814 for measuring the electrocardiogram when the automatic measurement and an electrode unit which has to be brought into contact with the user's body are selected during the measurement.

The mobile terminal according to FIG. 13B may include the electrode unit 724 provided at the stem portion. The controller may execute a specific function when a touch is applied to the stem portion or the stem portion is rotated or moved by an external force. For example, the controller may turn on the mobile terminal 600, switch the display unit 651 from an inactive state into an active state, or boot the mobile terminal 600, in response to an external force applied to the stem portion.

The controller may collect electrocardiogram information according to a potential difference, together with another electrode unit which is brought into contact with another portion of the user's body, when a finger is brought into contact with the electrode unit 724. The controller may control the display unit 651 to output a measurement screen 820 which indicates an ongoing measurement of biometric information for calculating a blood pressure value while executing a specific function corresponding to the stem portion.

The controller may control the display unit 651 to output blood pressure information 821 when the blood pressure value is calculated. The blood pressure information 821 may be output on an execution screen of a specific application or on one area of a home screen page.

The electrode unit 723 according to FIG. 13C may be disposed to surround at least one area of an edge of the display unit 651. According to this exemplary embodiment, a part (e.g., a hand) of the user's body can be more easily brought into contact with the electrode unit 723 while the mobile terminal 600 is worn.

The controller may enter a specific mode of the display unit 651 when a touch is applied with a palm of the user's hand to at least one area of the electrode unit 723. For example, the specific mode may correspond to a surrounding brightness mode for adjusting brightness of the display unit 651 according to surrounding brightness. When the display unit 651 is temporarily covered with the palm and then the palm is removed from the display unit 651, brightness of the display unit 651 may become darker. When the display unit 651 is covered for a preset period of time (several seconds), the controller may switch the mode of the display unit 651 into the surrounding brightness mode and change brightness of the display unit 651.

During the switching of the mode, the controller may collect biometric information from the user's body that is in a contact state with the electrode unit 723.

The controller may control the display unit 651 to output blood pressure information 820 which has been calculated based on the biometric information collected after the entry into the specific mode. The controller may prevent the output of the blood pressure information 820 while the surrounding mode is activated.

Figure 14:
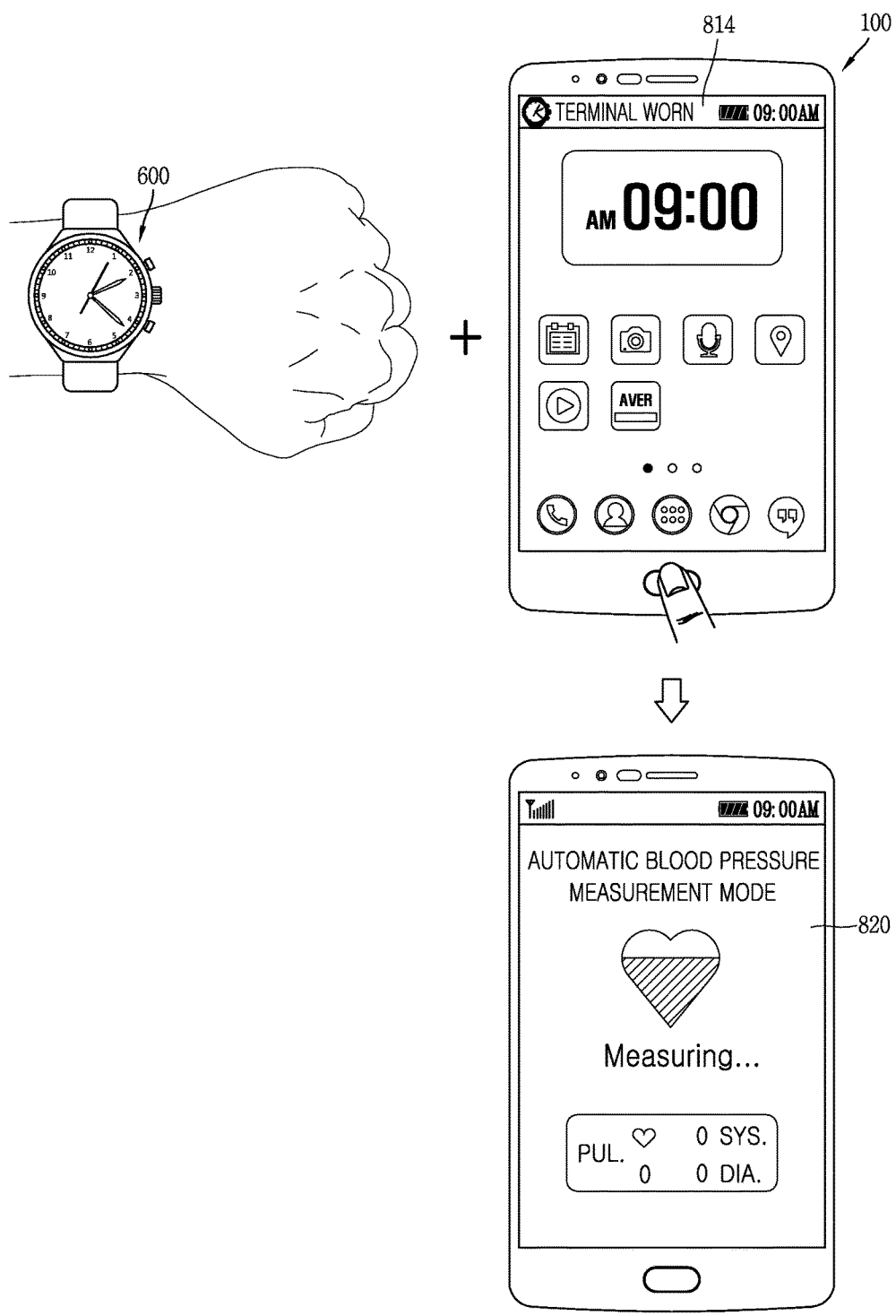
FIG. 14 is a conceptual view illustrating a method for controlling a mobile terminal in accordance with another exemplary embodiment.

FIG. 14 is a conceptual view illustrating a method for controlling a mobile terminal in accordance with another exemplary embodiment. A first mobile terminal 100 and a second mobile terminal 600 according to this exemplary embodiment may be wirelessly connected to each other. The controller of the first mobile terminal 100 may collect biometric information when it is sensed that the second mobile terminal 600 is worn on the user's wrist. Referring to FIGS. 11A, 11B and 14, the mobile terminal 100 according to this exemplary embodiment may include a first electrode unit provided with an electrode for collecting electrocardiogram information. The second mobile terminal 600 may include a light-emitting unit and a light-receiving unit for collecting pulse wave information, and a second electrode unit for collecting the electrocardiogram information along with the first electrode unit.

The second mobile terminal 600 may determine whether or not it has been worn on the user's wrist, by use of the light-emitting unit and the light-receiving unit. The controller of the second mobile terminal 600 may transmit a wireless signal to the first mobile terminal 100 when the second mobile terminal 600 is determined to have been worn on the user's wrist. When the wireless signal is received, the display unit of the first mobile terminal 100 may output notification information 814 for notifying the reception.

When the wireless signal is received, the controller of the first mobile terminal 100 may transmit a control signal to the second mobile terminal 600 such that the second mobile terminal 600 can collect pulse wave information using the light-emitting unit and the light-receiving unit. The first mobile terminal 100 may calculate a blood pressure value using the collected pulse wave information and electrocardiogram information. The display unit of the first mobile terminal 100 may output a measurement screen 820 which indicates the ongoing measurement of biometric information for calculating the blood pressure value.

According to this exemplary embodiment, when two mobile terminals are connected to each other in a wireless manner, a blood pressure measurement may be carried out without a separate control command. This may allow the user to obtain blood pressure which is measured without an intentional control command.

Figure 15:
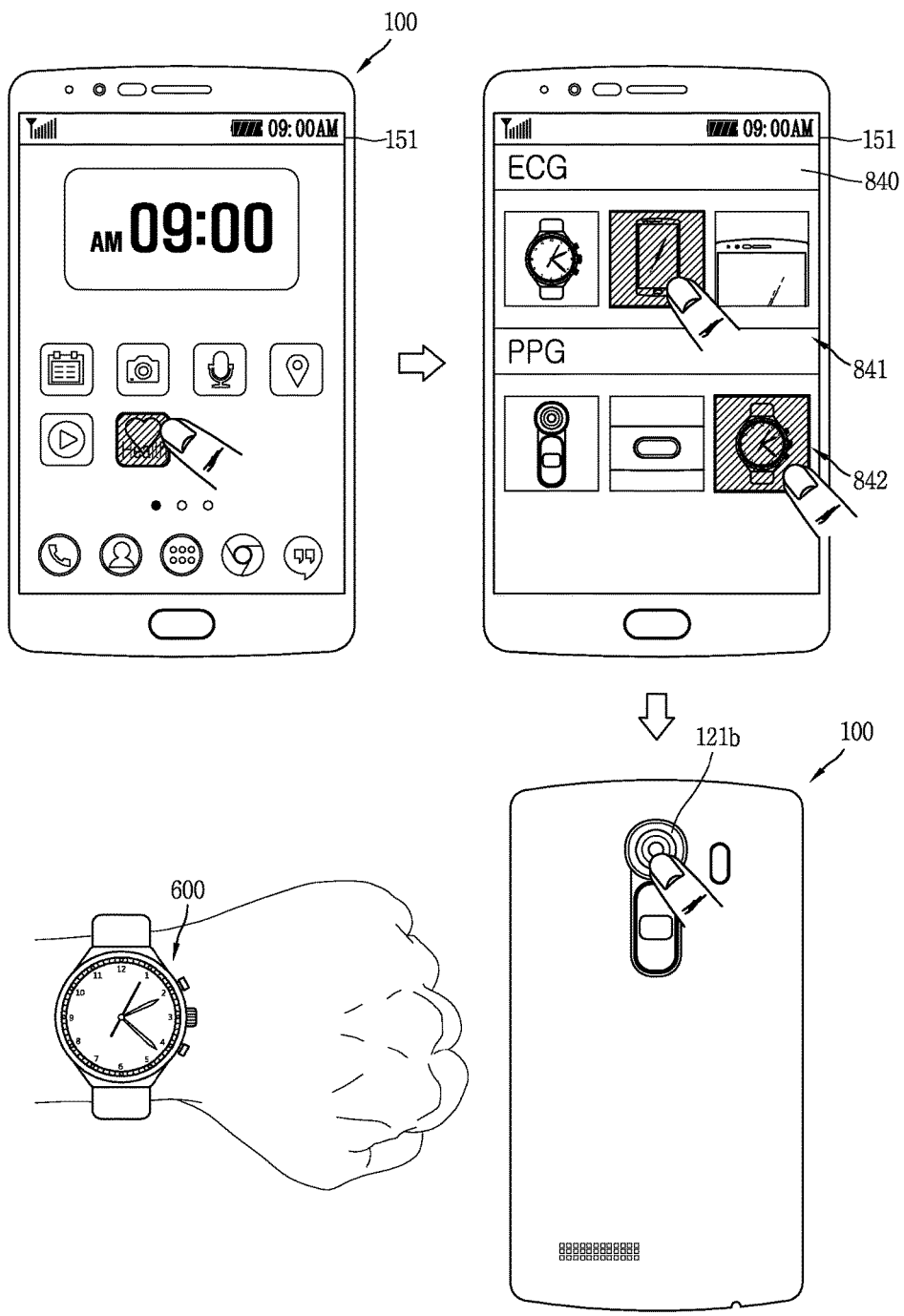
FIG. 15 is a conceptual view illustrating a control method of selecting a sensor for collecting biometric information.

FIG. 15 is a conceptual view illustrating a control method of selecting a sensor for collecting biometric information.

Referring to FIG. 15, the mobile terminal 100 may have an application which is installed to collect biometric information for measuring blood pressure and provide a blood pressure value calculated based on the biometric information or output related notification information.

The controller may control the display unit 151 to output an execution screen 840, which includes an ECG module select window 841 and a PPG sensor select window 842.

The mobile terminal 100 according to this exemplary embodiment may include a plurality of sensing members that collect biometric information for measuring blood pressure. The mobile terminal 100 may be wirelessly connectable with an external device for collecting the biometric information.

For example, the controller may select a PPG sensor and an electrode unit included in an external device 600, and an electrode unit disposed adjacent to the camera 121b of the mobile terminal 100. Therefore, when the mobile terminal 100 includes a plurality of sensors, the user can collect biometric information through a sensor located at a desired position according to convenience of use.

Examples of such external devices include cellular phones, smart phones, user equipment, laptop computers, digital broadcast terminals, personal digital assistants (PDAs), portable multimedia players (PMPs), navigators, slate PCs, tablet PCs, ultra books, wearable devices (for example, smart watches, smart glasses, head mounted displays (HMDs)), and the like.

The present invention can be implemented as computer-readable codes in a program-recorded medium. The computer-readable medium may include all types of recording devices each storing data readable by a computer system. Examples of such computer-readable media may include hard disk drive (HDD), solid state disk (SSD), silicon disk drive (SDD), ROM, RAM, CD-ROM, magnetic tape, floppy disk, optical data storage element and the like. Also, the computer-readable medium may also be implemented as a format of carrier wave (e.g., transmission via an Internet). The computer may include the controller 180 of the terminal. Therefore, it should also be understood that the above-described embodiments are not limited by any of the details of the foregoing description, unless otherwise specified, but rather should be construed broadly within its scope as defined in the appended claims, and therefore all changes and modifications that fall within the metes and bounds of the claims, or equivalents of such metes and bounds are therefore intended to be embraced by the appended claims.

What is claimed is:

1. A mobile terminal comprising:
a user input unit for receiving a control command for executing an authentication procedure;
a sensor formed integrally with the user input unit, the sensor comprising a light-emitting unit a light-receiving unit, and a pressure sensor capable of sensing an external force; and
a controller configured to:
execute the authentication procedure in response to the control command;
activate the sensor to emit light and receive light reflected from a portion of a user's finger in response to the same control command; and
generate a blood pressure value based on the received light obtained via the activated sensor,
wherein:
the control command is generated when the user input unit is touched by the portion of the user's finger such that fingerprint information of the user is sensed by the sensor for the authentication procedure;
the light-emitting unit is configured to emit the light to collect pulse wave information for generating the blood pressure value;
the light-receiving unit is configured to receive the light reflected from the portion of the user's finger; and
the controller is further configured to generate the blood pressure value based on pressure sensed by the pressure sensor and the pulse wave information corresponding to the sensed pressure when the fingerprint information matches a pre-stored fingerprint image.

2. The terminal of claim 1, wherein:
the control command is received while the terminal is in a lock mode; and
the controller is further configured to release the lock mode based on the fingerprint information sensed during the authentication procedure.

3. The terminal of claim 2, further comprising a display, wherein the controller is further configured to cause the display to display guide information when the control command is received via the user input unit, the guide information notifying that biometric information is being obtained.

4. The terminal of claim 1, further comprising a memory, wherein the controller is further configured to cause the memory to store the blood pressure value and information related to the blood pressure value.

5. The terminal of claim 4,
wherein the controller is further configured to cause the memory to store the fingerprint image of the user.

6. The terminal of claim 1, wherein
the controller is further configured to collect the pulse wave information via the sensor while the fingerprint information is sensed by the sensor.

7. The terminal of claim 6, wherein no additional control command is required to be received via the user input unit for the sensor to sense the fingerprint information and at the same time to be activated to collect the pulse wave information.

8. The terminal of claim 1, further comprising a display, wherein the controller is further configured to cause the display to display a guide image for guiding pressure to be applied to the sensor.

9. The terminal of claim 1, wherein the sensor further comprises:
a first electrode unit located adjacent to an audio output module, through which audio information is output when a call function is executed, and configured to collect electrocardiogram information;
a second electrode unit configured to collect the electrocardiogram information; and
a photo plethysmo gram (PPG) sensor configured to sense the pulse wave information.

10. The terminal of claim 1, wherein the controller is further configured to sense the pulse wave information and electrocardiogram information via the sensor while the control command is received via the user input unit when an alarm is output.

11. The terminal of claim 1, wherein:
the sensor further comprises:
a fingerprint sensing portion provided with an Rx area and a Tx area and configured to sense the fingerprint information;
an electrode unit; and
a photo plethysmo gram (PPG) sensor; and
the controller is further configured to measure electrocardiogram information according to a potential difference based on the Tx area and the electrode unit, in response to the control command.

12. The terminal of claim 1, further comprising a wireless communication unit,
wherein the controller is further configured to:
perform wireless communication with a wearable terminal having a photo plethysmo gram (PPG) sensor and an electrode unit via the wireless communication unit; and
obtain biometric information sensed by the PPG sensor when a signal for notifying a worn state of the wearable terminal is received via the wireless communication unit from the wearable terminal.

13. The terminal of claim 1, further comprising a display, wherein the sensor comprises a plurality of sensors disposed at different areas of a body of the terminal, and
wherein the controller is further configured to cause the display to display an execution screen including a window for selecting at least part of the plurality of sensors.

14. A method for controlling a mobile terminal, the method comprising:
receiving a control command for executing an authentication procedure via a user input unit;
executing the authentication procedure in response to the control command;
activating a sensor to emit light and receive light reflected from a portion of a user's finger in response to the same control command, the sensor comprising a light-emitting unit, a light-receiving unit, and a pressure sensor capable of sensing an external force; and
generating a blood pressure value based on the received light obtained via the activated sensor, wherein:
the control command is generated when the user input unit is pushed or touched by the portion of the user's finger such that fingerprint information of the user is sensed by the sensor for the authentication procedure;
the light is emitted by the light-emitting unit to collect pulse wave information for generating the blood pressure value;
the light reflected from the portion of the user's finger is received by the light-receiving unit; and
the blood pressure value is generated based on pressure sensed by the pressure sensor and the pulse wave information corresponding to the sensed pressure when the fingerprint information matches a pre-stored fingerprint image.

15. The method of claim 14, wherein the specific function is executed after the biometric information is obtained.

16. The method of claim 15, further comprising:
displaying guide information for notifying that the biometric information is being obtained when the control command is received via the user input unit.

17. The method of claim 14, further comprising:
executing the specific function when a fingerprint sensed by the sensor matches a prestored fingerprint image, the fingerprint sensed when the control command is received via the user input unit.

18. The method of claim 14, wherein:
the specific function corresponds to an alarm output function; and
the method further comprises sensing pulse wave information and electrocardiogram information while the control command is received via the user input unit when an alarm is output.

19. The method of claim 14, further comprising:
performing wireless communication with a wearable terminal having a photo plethysmo gram (PPG) sensor and an electrode unit; and
obtaining second biometric information sensed by the PPG sensor when a signal for notifying a worn state of the wearable terminal is received from the wearable terminal.

* * * * *